US012263144B2

(12) United States Patent
Jin

(10) Patent No.: US 12,263,144 B2
(45) Date of Patent: Apr. 1, 2025

(54) METHODS OF TREATING IGA NEPHROPATHY WITH THIOL-CONTAINING MOLECULES

(71) Applicant: Accubit LLC—Biotechnology, Chicago, IL (US)

(72) Inventor: Jing Jin, Chicago, IL (US)

(73) Assignee: Accubit LLC—Biotechnology, Chicago, IL (US)

( * ) Notice: Subject to any disclaimer, the term of this patent is extended or adjusted under 35 U.S.C. 154(b) by 492 days.

(21) Appl. No.: 17/500,625

(22) Filed: Oct. 13, 2021

(65) Prior Publication Data

US 2022/0110894 A1    Apr. 14, 2022

Related U.S. Application Data

(60) Provisional application No. 63/090,902, filed on Oct. 13, 2020.

(51) Int. Cl.
A61K 31/145 (2006.01)
A61P 13/12 (2006.01)
G01N 33/68 (2006.01)

(52) U.S. Cl.
CPC ....... A61K 31/145 (2013.01); G01N 33/6854 (2013.01)

(58) Field of Classification Search
CPC ............. A61K 31/145; G01N 33/6854; G01N 2500/20; A61P 13/12
See application file for complete search history.

(56) References Cited

U.S. PATENT DOCUMENTS

| | | | |
|---|---|---|---|
| 9,468,612 | B2 | 10/2016 | Eddy et al. |
| 2014/0315786 | A1* | 10/2014 | Jirousek ................ A61K 31/455 514/1.5 |
| 2017/0189525 | A1* | 7/2017 | Brunskill ................ A61P 13/12 |
| 2019/0038747 | A1 | 2/2019 | Pinter et al. |
| 2019/0092851 | A1 | 3/2019 | Myette et al. |
| 2019/0292157 | A1 | 9/2019 | Casimiro-Garcia et al. |
| 2020/0223905 | A1 | 7/2020 | Palese et al. |
| 2021/0364500 | A1 | 11/2021 | Jin et al. |

FOREIGN PATENT DOCUMENTS

| | | | | |
|---|---|---|---|---|
| WO | WO-2013062544 | A1 * | 5/2013 | ........... A61K 31/145 |
| WO | 2014/071456 | A1 | 5/2014 | |

OTHER PUBLICATIONS

Batra, R., H. Chan, G. Kamath, R. Ramprasad, M. Cherukara and S. Sankaranarayan, J. Phys. Chem. Lett. (2020), 11: pp. 7058-7065. (Year: 2020).*
Davita Kidney Care, IgA Nephropathy (Berger's Disease), The Wayback Machine—https://web.archive.org/web/20200928200447/https://www.davita.com /education/kidney-disease/related-diseases/iga-nephropathy-bergers-disease, Available online: Sep. 28, 2020. (Year: 2020).*
Xie, X., et al., "Propensity of IgA to Self-Aggragate via Tailpiece Cysteine-471 and Treatment of IgA Nephropathy Using Cysteamine", JCI Insight, Oct. 8, 2021, vol. 6(19), Article e150551, pp. 1-10. (Year: 2021).*
Liu, et al., "Novel ACE2-Fc Chimeric Fusion Provides Long-Lasting Hypertension Control and Organ Protection in Mouse Models of Systemic Renin Angiotensin System Activation", Kidney Int., 2018, vol. 94(1), pp. 114-125.
Booth, D.S., et al., "Visualizing Proteins and Macromolecular Complexes by Negative Stain EM: from Grid Preparation to Image Acquisition", J. Vis. Exp. and FEI, Dec. 2011, Issue 58, e3227, pp. 1-7.
Barratt, J., et al., "Immunopathogenesis of IgAN", Semin. Immunopathol., 2007, vol. 29(4), pp. 427-443.
Brunke, C., et al., "Effect of a Tail Piece Cysteine Deletion on Biochemical and Functional Properties of an Epidermal Growth Factor Receptor-Directed IgA2m(1) Antibody", MAbs., 2013, vol. 5(6), pp. 936-945.
Fallgreen-Gebauer, E., et al., "The Covalent Linkage of Secretory Component to IgA. Structure of sIgA", Biol. Chem. Hoppe Seyler, Nov. 1993, vol. 374(11), pp. 1023-1028.
Gahl, W.A., et al., "Cystinosis", N. Engl. J. Med., 2002, vol. 347(2), pp. 111-121.
Hui, G.K., et al., "The Solution Structures of Native and Patient Monomeric Human IgA1 Reveal Asymmetric Extended Structures: Implications for Function and IgAN Disease", Biochem. J., 2015, vol. 471(2), pp. 167-185.
King, M., et al., "Use of Amifostine for Cytoprotection during Radiation Therapy: A Review", Oncology, Dec. 2019, vol. 98(2), pp. 61-80.
Kokubo, T., et al., "Protective Role of IgA1 Glycans Against IgA1 Self-Aggregation and Adhesion to Extracellular Matrix Proteins", J. Am. Soc. Nephrol., 1998, vol. 9(11), pp. 2048-2054.
Korst, A.E., et al., "Pharmacokinetics of Amifostine and its Metabolites in Patients", Eur. J. Cancer, 1997, vol. 33(9), pp. 1425-1429.
MacLaren, J.A., et al., "The Oxidation of Disulphide Groups in Proteins", Biochim. Biophys. Acta., 1959, vol. 35, pp. 280-281.
Maruoka, T., et al., "Identification of the Rat IgA Fc Receptor Encoded in the Leukocyte Receptor Complex", Immunogenetics, 2004, vol. 55(10), pp. 712-716.
Mestecky, J., et al., "IgA Nephropathy: Molecular Mechanisms of the Disease", Annu. Rev. Pathol. Mech. Dis., 2013, vol. 8, pp. 217-240.
O'Brian, C.A., et al., "Post-Translational Disulfide Modifications in Cell Signaling-Role of Inter-Protein, Intra-Protein, S-glutathionyl, and S-cysteaminyl Disulfide Modifications in Signal Transmission", Free Radic. Res., 2005, vol. 39(5), pp. 471-480.

(Continued)

Primary Examiner — Samantha L Shterengarts
Assistant Examiner — Sagar Patel
(74) Attorney, Agent, or Firm — McDonnell Boehnen Hulbert & Berghoff LLP

(57) ABSTRACT

A method for treatment or preventing IgA nephropathy in a subject is provided. The method of treating or preventing IgA nephropathy includes administering a thiol-containing molecule, or a pharmaceutically acceptable salt thereof, to a mammal in need thereof. Also provided is a method and kit for screening candidate therapeutic agents for treating or preventing IgA nephropathy.

12 Claims, 20 Drawing Sheets

Specification includes a Sequence Listing.

(56) References Cited

OTHER PUBLICATIONS

Suzuki, H., et al., "The Pathophysiology of IgA Nephropathy", J. Am. Soc. Nephrol., 2011, vol. 22(10), pp. 1795-1803.
Suzuki, H., et al., "Aberrantly Glycosylated IgA1 in IgA Nephropathy Patients is Recognized by IgG Antibodies with Restricted Heterogeneity", J. Clin. Invest., 2009, vol. 119(6), pp. 1668-1677.
Tomasi, T.B., "The Discovery of Secretory IgA and the Mucosal Immune System", Immunol. Today, 1992, vol. 13 (10), pp. 416-418.
Wang, Y., et al., "Structural Insights into Secretory Immunoglobulin A and its Interaction with a Pneumococcal Adhesin", Cell Res., 2020, vol. 30(7), pp. 602-609.
Wang, L., et al., "Bacterial IgA Protease-Mediated Degradation of aglgA1 and aglgA1 Immune Complexes as a Potential Therapy for IgA Nephropathy", Nature Sci. Rep., 2016, vol. 6, article 30964.
Wyatt, R.J., et al., "IgA Nephropathy", N. Engl. J. Med., 2013, vol. 368(25), pp. 2402-2414.
Xie X., et al., "Renal Deposition and Clearance of Recombinant Poly-IgA Complexes in a Model of IgA Nephropathy", J. Pathol., Apr. 9, 2021, vol. 254, pp. 159-172.
Zhang, J.J., et al., "Binding Capacity of in vitro Deglycosylated IgA1 to Human Mesangial Cells", Clin. Immunol., 2006, vol. 119(1), pp. 103-109.
Xie, X., et al., "Propensity of IgA to Self-Aggregate via Tailpiece Cysteine-471 and Treatment of IgA Nephropathy using Cysteamine", JCI Insight, Oct. 8, 2021, vol. 6 (19), e150551, pp. 1-10.
Korst, A.E., et al., "Pharmacokinetics of Cisplatin With and Without Amifostine in Tumour-Bearing Nude Mice", European Journal of Cancer, 1998, vol. 34(3), pp. 412-416.
Kurano, M., et al., "Use of Gas Chromatography Mass Spectrometry to Elucidate Metabolites Predicting the Phenotypes of IgA Nephropathy in Hyper IgA Mice", PLoS One, Jul. 10, 2019, vol. 14(7), pp. 1-14.
Trascasa, M.L., et al., "IgA Glomerulonephritis (Berger's Disease): Evidence of High Serum Levels of Polymeric gA", Clinical & Experimental Immunology, Nov. 1, 1980, vol. 42(2), pp. 247-254.
Xie, X., et al., "Propensity of IgA to Self-Aggregate via Tailpiece Cysteine-471 and Treatment of IgA Nephropathy Using Cysteamine", JCI Insight, Oct. 8, 2021, vol. 6(19), Article e150551, pp. 1-10.
International Search Report and Written Opinion from the International Searching Authority, for International Application No. PCT/US2021/054794, mailing date of Jan. 18, 2022, pp. 1-50.
Ai, K.N., et al., "IgA Nephropathy", Nat. Rev. Dis. Primers, Feb. 11, 2016, vol. 2, Article 16001, pp. 1-20.

\* cited by examiner

METHODS OF TREATING IGA NEPHROPATHY WITH THIOL-CONTAINING MOLECULES

CROSS-REFERENCE TO RELATED APPLICATIONS

This application claims the benefit of priority of U.S. Provisional Application No. 63/090,902, filed Oct. 13, 2020, and incorporated herein by reference in its entirety.

REFERENCE TO A SEQUENCE LISTING

The instant application contains a Sequence Listing which has been submitted electronically as a text file in ASCII format and is hereby incorporated by reference in its entirety. Said ASCII copy, created on Oct. 12, 2021, is named "20-1581-US_Sequence-Listing_ST25.txt" and is 19 kb in size.

FIELD

The present disclosure provides a method for treating or preventing IgA nephropathy in mammals using thiol-containing molecules. The present disclosure also provides a method and kit for screening therapeutic agents for treating or preventing IgA nephropathy.

BACKGROUND

IgA nephropathy (IgAN), also known as Berger's disease, is the most common form of glomerular nephritis, affecting 40-50% of all biopsy diagnoses in Asia. In most IgA nephropathy cases, the disease slowly progresses while causing gradually decreasing kidney function, with poorer outcomes among Asian patents. It is estimated that up to 30-40% patients will eventually develop end-stage renal disease (ESRD) that requires renal replacement therapy, including dialysis and/or kidney transplantation. IgA nephropathy occurs where polymeric immunoglobulin A (IgA) is deposited in the glomerular mesangium of the kidney as a manifestation of an underlying autoimmune disorder. IgA deposits cause chronic inflammation of the kidney and impairment of glomerular filtration, leading to renal insufficiency of patients. These patients experience buildup of fluid and toxic waste in the body, which may cause edema in the patient's extremities, high blood pressure, electrolyte imbalance, and even severe life-threatening conditions such as multi-organ failure. Because the exact cause of IgA deposition in the glomerulus remains unknown, there is no specific treatment for IgA nephropathy at the current time. Instead, following diagnosis, conventional therapy involves treatment with blood pressure-control medications. In some rapidly progressive forms of IgA nephropathy, immunosuppressant therapies such as the use of corticosteroids are prescribed. However, clinical trials of these aggressive treatments has not reached definitive conclusions about treatment benefit due to an increased risk of serious adverse events associated with corticosteroid usage. Despite the prevalence of IgA nephrophaty, the molecular mechanisms underlying IgA deposition in the glomerulus remain elusive and specific treatments of the disease are currently unavailable. Hence, there is an unmet need for new treatments that can effectively alleviate IgA nephropathy and prevent or delay onset of complications associated thereof. Further, there is a need for methods for treating or preventing IgA nephropathy as well as methods and kits to facilitate the development and the preclinical validation of new therapeutic agents for treatments and for preventing IgA nephropathy.

SUMMARY

The present disclosure concerns methods of treating or preventing IgA nephrophathy as well as in vitro models associated with drug discovery. It has been determined that particular thiol-containing compounds can inhibit aberrant poly-IgA formation without disrupting normal protein functioning. These compounds present a promising path towards further understanding and treating IgA nephropathy.

One aspect of the present disclosure is a method of treating or preventing IgA nephropathy in mammals, the method including administering a therapeutically effect amount of a thiol-containing molecule or a pharmaceutically acceptable salt thereof to a mammal in need thereof.

In particular embodiments, the thiol-containing molecule is cysteamine, 2-((3-aminopropyl)amino]ethanethiol, or N-acetylcysteine.

In another aspect, the present disclosure provides for a method for inhibiting poly-IgA formation, the method comprising administering to a solution of IgA monomers a thiol containing molecule.

In another aspect, the present disclosure provides for a method for screening for therapeutic agent candidates, the method comprising;
  providing a sample comprising poly-IgA;
  admixing the sample with a therapeutic agent candidate;
  determining the percent conversion of poly-IgA into monomeric-IgA.

In another aspect, the present disclosure provides for a kit for screening candidate therapeutic agents, the kit comprising:
  a container comprising a predetermined amount of poly-IgA, wherein the poly-IgA is provided as a solution, suspension, or solid; one or more optional buffers; and instructions for use of the kit.

Other aspects of the disclosure will be apparent to those skilled in the art in view of the description that follows.

DETAILED DESCRIPTION

Figure 1:
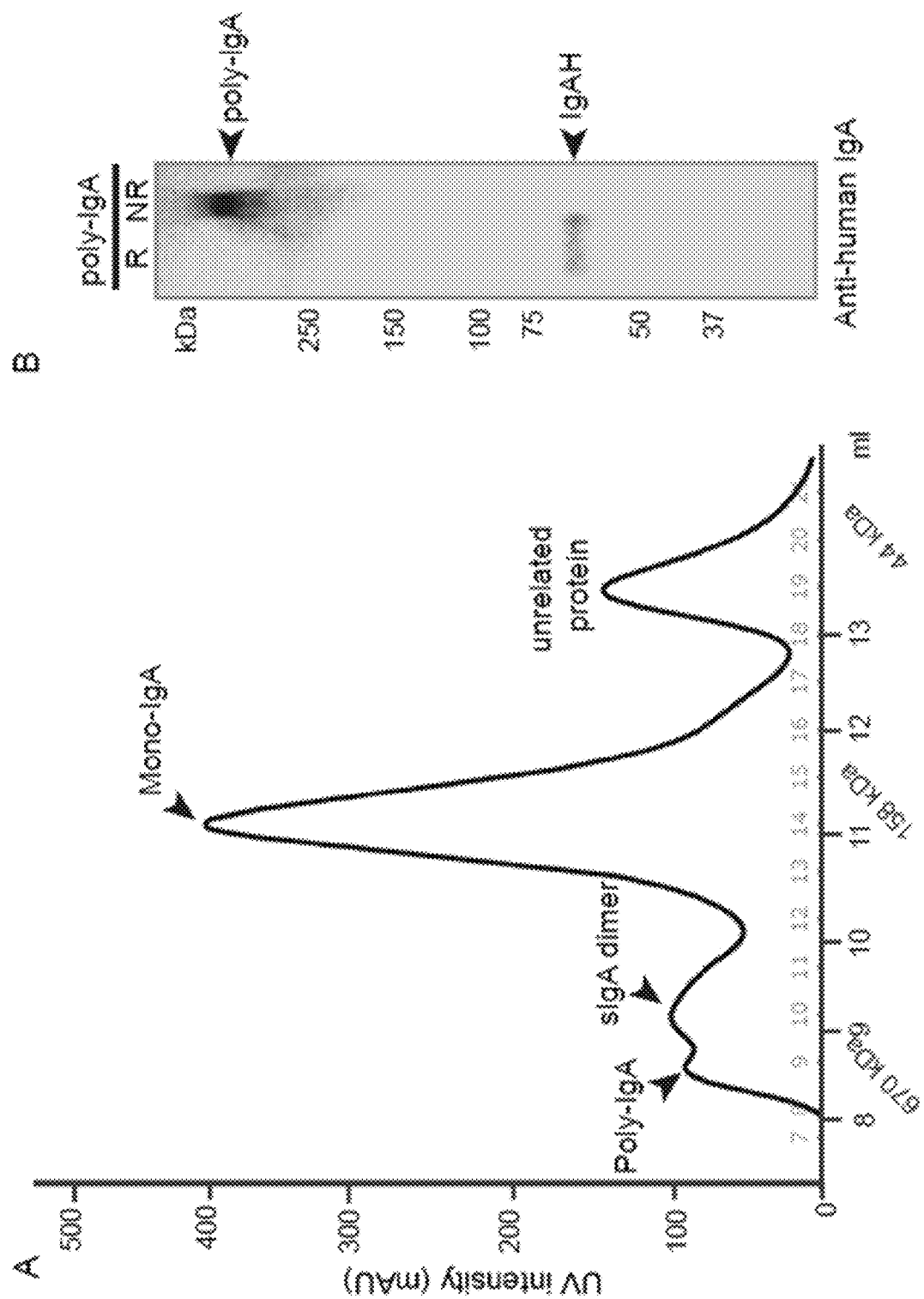
FIG. 1: IgA nephropathy patients' plasma contains poly-IgA complexes that are susceptible to reducing agent tris (2-carboxyethyl)phosphine (TCEP). A. Pooled plasma samples were collected from IgA nephrophathy patients (n=10), and total IgA1 was extracted using jacalin-conjugated column. The extraction was then resolved by SEC, which was calibrated against molecular weight standards (arrowheads: kDa vs elution volume along x-axis). The IgA contents formed one major peak of mono-IgA, preceded by several overlapping minor peaks of poly-IgA and dimeric sIgA. B. The poly-IgA fraction was subsequently analyzed by Western blotting with anti-human IgA heavy chain antibody under either reducing (R: with TCEP) or non-reducing (NR: without TCEP) condition. With the addition of TCEP, the ~600 kDa poly-IgA complexes were reduced to a ~65 KDa band of IgA heavy chain (IgAH).

IgA nephropathy is the most common form of primary glomerulonephritis and a leading cause of end-stage kidney disease (ESKD). IgA nephropathy is thought to result from improper polymerization of IgA proteins, resulting in buildup in the kidneys through chronic deposition of poly-IgA complexes in the glomerular mesangium, causing inflammatory injuries to the kidney. It is generally believed that certain forms of IgA molecules in blood circulation are prone to aggregate into poly-IgA complexes, either through self-association (see, e.g., FIG. 1-FIG. 4) or through anti-glycan antibodies against O-glycosylated epitopes on IgA1. If not cleared by the liver promptly, poly-IgA can deposit in the mesangial areas of the kidney glomerulus. In this disclosure, experiments were conducted that demonstrate that an amino acid (known as the penultimate Cys471 residue) on the "tail piece" segment of the IgA heavy chain can form intermolecular disulfide bridges between IgA molecules (FIG. 6, FIG. 7), promoting the formation of poly-IgA.

It was noted that high molecular weight poly-IgA complexes contain aberrant O-linked glycosylation of the hinge region of IgA1 heavy chain. Also, glycoforms with reduced galactose contents are associated with higher incidence of IgA nephropathy. In-solution X-ray scattering data showed that IgA1 is prone to non-specific self-association when levels of O-galactosylation is reduced, in keeping with the notion that O-glycans protect IgA1 from self-aggregation, and/or adhesion to matrices. It was also suggested that these aberrant glycoforms, referred to as galactose-deficient IgA1 (Gd-IgA1), are antigenic. In IgA nephropathy patients, anti-Gd-IgA1 autoantibodies of IgG or IgM can be detected, and these IgG-IgA1 and IgM-IgA1 antibody-antigen pairs may lead to the formation of poly-IgA immune complexes in circulation that are susceptible to renal deposition.

Besides glycosylation on IgA1 hinge segment, another important feature of IgA molecule is that both IgA1 and IgA2 isotypes have secretory and non-secretory forms. Secretory IgA (sIgA) has two IgA monomers linked by two additional polypeptide subunits, namely the J-chain and the secretory component (SC). It is important to note that J-chain and SC form cysteine-to-cysteine disulfide bridges with IgA heavy chain in the sIgA configuration. Specifically, J-chain's Cys14 and Cys68 residues form two separate disulfide bonds with Cys471 in the so-called secretory tailpiece (tp) of IgA heavy chain to bridge two IgA molecules. SC, on the other hand, forms disulfide bond with Cys311 in CH2 domain of IgA heavy chain. In non-secretory IgA1 monomer, which predominates in plasma, Cys311 and Cys471 residues are not connected to SC and J-chain, and therefore maintain their reduced and free forms. Under oxidative conditions, these free cysteines are prone to form disulfide bonds with other cysteine residues that potentially coalesce IgA into high-order molecular aggregates. Our study investigated the propensity of free Cys311 and Cys471 of human IgA1 in promoting self-aggregation, as well as therapeutic means to disaggregate IgA complexes using thiol-reactive drugs.

There are a wide range of systemic diseases and localized conditions that can cause kidney dysfunctions and diseases. In general, antioxidants are known to be protective against oxidation and inflammation, which can attenuate nephrotoxicity. However, and without wishing to be bound by theory, this is a distinct protective mechanism from the mechanism-of-action of cysteamine, WR-1065 (also referred to as 2-[(3-aminopropyl)amino]ethanethiol), or N-acetylcysteine as disclosed herein in disassembling poly-IgA complexes and therefore reducing IgA deposition in the kidney, which is the root cause of IgA nephropathy. The experimental data disclosed herein surprisingly demonstrate that the thiol group of cysteamine does not act as a mere redox reactant, but rather specifically reacts with Cys-471 residue of the IgA heavy chain, and thereby prevents it from forming unwanted intermolecular disulfide bonds in aggregating IgA. Similarly, it is demonstrated that two other thiol-reactive compounds, WR-1065 and N-acetylcysteine (NAC), are also surprisingly effective in reducing pathogenic poly-IgA levels and therefore represent promising therapeutic agents in the treatment of IgA nephropathy.

As used herein, treating IgA nephropathy may refer to therapy that removes or reduces the amount of existing poly-IgA aggregation in kidney tissue. Additionally or alternatively, treating IgA nephropathy may refer to preventing additional deposits of poly-IgA from forming in kidney tissue, or preventing poly-IgA formation.

This is in contrast to reducing thiol compound glutathione that showed relatively modest effects on poly-IgA levels when used with comparable concentrations, suggesting that different thiol compounds have different potency against poly-IgA aggregates. Therefore, selecting compounds with desired reducing efficacy is critical for treatment use, as TCEP and DTT were shown below to be too potent in our ex vivo study that also inadvertently dissociated normal pairing of IgA heavy chains, while cysteamine, WR-1065 and N-acetylcysteine did not cause unwanted disruption of natural IgA1 assembly (comprised of two heavy chains and two light chains connected via disulfide bonds).

As discussed herein, several suitable thiol-containing molecules have been identified, wherein the thiol-containing molecule is understood to be a molecule that comprises at least one thiol (i.e. —SH) moiety. Critically, the thiol-containing molecule must have sufficient activity to inhibit poly-IgA function, but not interfere with normal IgA functionality. Surprisingly, as disclosed herein, a particular class of compounds that meets these criteria has been identified. Accordingly, in certain embodiments as otherwise described herein, the thiol-containing molecule comprises at least one amino group. For example, in particular embodiments, the thiol-containing molecule comprises one or two amino group (e.g., wherein each amino group is either primary or secondary).

The amino groups as otherwise described herein may be neutral (e.g., —$NH_2$ or —NH—) or hypervalent as a suitable salt (e.g., —$NH_3^+$ or —$NH_2^-$'). For example, the thiol-containing molecule may be present as a pharmaceutically acceptable salt thereof, wherein one or more of the amino groups are optionally hypervalent. Additionally or alternatively, a carboxy group, if present, may be protonated and neutral, or deprotonated as a monoanionic moiety.

In particular embodiments, the thiol-containing molecule has one or two thiol groups. For example, in certain embodiments, the thiol-containing molecular comprises exactly one thiol.

The proximity of the amino group and the thiol group may play an important role in drug functionality. Accordingly, in certain embodiments as otherwise described herein, a thiol of the thiol-containing molecule is bound to at least one amino group through an ethylene bridge (i.e., a divalent $C_2$ alkyl group). In certain embodiments, the ethylene bridge is unsubstituted. In other embodiments, the ethylene bridge may be substituted by a carboxy group.

Accordingly, in certain embodiments as otherwise described herein, the thiol-containing molecule is selected from the group consisting of cysteamine, WR-1065 (i.e., 2-[(3-aminopropyl)amino]ethanethiol), and N-acetylcysteine (i.e., N-acetyl-L-cysteine). For example, in particular embodiments, the thiol-containing molecule is cysteamine or N-acetylcysteine (NAC).

IgA may be either native IgA purified from plasma, or synthetic analogs in the form of rIgA that contains the Fc segment of IgA heavy chain. Both native and synthetic analog IgAs have a natural tendency to form poly-IgA aggregates in solution.

To counter this aberrant polymerization, ex vivo studies discussed in the Examples below have surprisingly shown a dose dependent sensitivity of poly-IgA, either in the form of native or synthetic analogs such as recombinant IgA/rIgA, to reducing agents, such as TCEP (tris(2-carboxyethyl)phosphine) as well as other thiol-containing molecules, such as cysteamine. Cysteamine is of special interest as it is already an FDA approved drug to treat cystinosis by dissolving cystine crystals. Accordingly, in certain embodiments, the method of treating or preventing IgA nephropathy comprises the thiol-containing molecule binding with an IgA monomer, while having desired potency that does not disrupt normal assemblies of IgA and other nature protein complexes to cause adverse drug effects.

As disclosed herein, it has been found that certain thiol-containing molecules, such as cysteamine, are able to convert aberrantly formed poly-IgA to monomeric IgA (comprised of two heavy chains and two light chains) in a dose-dependent manner, and can also effectively reduce, and/or prevent, IgA aggregation and thus is useful for treating IgA nephropathy. Additionally, it has been determined that intravenous injection of poly-rIgA, purified through size-exclusion chromatography, in rats causes glomerulus deposition of IgA. In contrast, administration of cysteamine prior to intravenous poly-IgA injection prevented IgA deposition in kidney glomeruli. The resulting poly-IgA treatment produced an animal model useful for evaluating IgA nephropathy treatments. Furthermore, the animal model established that certain thiol-containing molecules can be useful for treating or preventing IgA nephropathy.

The thiol-containing molecule as otherwise described herein may be administered to a wide variety of mammalian subjects. For example, in certain embodiments, the mammal is selected from the group consisting of human, rat, mouse, dog, monkey, chimpanzee, and rabbit.

In another aspect, the present disclosure provides for a method for inhibiting polyIgA formation, the method comprising administering to a solution comprising IgA monomers a thiol-containing molecule. For example, the thiol-containing molecule as otherwise described herein.

In another aspect, the present disclosure provides for a method for screening for therapeutically effective agents, the method comprising:
 providing a sample comprising poly-IgA;
 admixing the sample with an agent of interest;
 determining the percent conversion of poly-IgA into monomeric-IgA.

For example, the agent of interest may be a thiol-containing molecule as otherwise described herein. Alternatively, the method for screening as otherwise described herein may, in certain embodiments, be utilized to identify novel classes of molecules that are therapeutically effective. The sample can include recombinant poly-IgA, poly-IgA obtained from the bodily fluid, e.g., blood or blood component (e.g., plasma) of a patient or generated from IgA by subjecting IgA to a procedure, e.g., chemical oxidative procedure. The sample can include any suitable aqueous liquids such as one or more buffers or saline to suspend, admix or dissolve the poly-IgA.

In another aspect, the present disclosure provides for a kit for screening candidate therapeutic agents, the kit comprising:
 a container comprising a predetermined amount of poly-IgA, wherein the poly-IgA is provided as a solution, suspension, or solid;
 one or more optional buffers; and
 instructions for use of the kit.

Suitable examples of buffers include saline, citrate-based buffer, and phosphate-based buffers, such as PBS. Suitable examples of containers include vials or bottles. The poly-IgA may be prepared from native IgA purified from plasma, or synthetic analogs in the form of rIgA that contains the Fc segment of IgA heavy chain. Both native and synthetic analog IgAs have a natural tendency to form poly-IgA in solution. Purified poly-IgA may be purified by any method as known in the art, such as through size exclusion chromatography. The poly-IgA included in the kit as otherwise described herein may be provided in any suitable form. For example, in certain embodiments as otherwise described herein, the poly-IgA is dissolved in solution, for example, a buffer solution. In other embodiments, the poly-IgA is at least partially precipitated out of solution, and so is provided as a suspension. In further embodiments, the poly-IgA may be isolated as a solid powder. In such embodiments, the kit may further comprise a buffer solution that may be used to reconstitute the poly-IgA for use. Alternatively, the kit may comprise instructions for preparing a suitable buffer solution for use of the poly-IgA.

As discussed further in the Examples, it has been determined that the effectiveness of certain agents for preventing or treating poly-IgA, deposition may be observed in mammals. For example, in certain embodiments as otherwise described herein, the method further comprises determining the amount of poly-IgA deposition. This may be conducted through techniques known in the art. For example, in particular embodiments, the determining the amount of poly-IgA deposition is performed through kidney imaging, optionally through immunofluorescence imaging.

The compounds as otherwise described herein may not only be useful in the treatment of poly-IgA deposits, but may also function to prevent such deposits as well. Accordingly, in another aspect, the present disclosure provides for a method of preventing IgA nephropathy in a mammal, the method comprising administering a therapeutically effect amount of a thiol-containing molecule, or a pharmaceutically acceptable salt thereof. For example, the thiol-containing molecule may be that as otherwise described herein.

Advantageously, cysteamine is readily available in the forms of oral medication (in capsule and extended release formulations), and also in eye drops. In certain embodiments as otherwise described herein, cysteamine is provided in a commercially available form, for example, those sold under the trade names Cystagon® (Mylan), or Procysbi® (Horizon Therapeutics), or Cystaran® (Leadiant Biosciences).

WR-1065 (2-[(3-aminopropyl)amino]ethanethiol) is a metabolite and active form of Amifostine (ethiofos: brand name: Ethyol®), an approved drug for reducing renal toxicity with chemotherapy and for moderate to severe xerostomia from radiation therapy.

N-acetylcysteine is available as a common oral supplement and used to treat acetaminophen overdose, and may be obtained from Sigma-Aldrich.

The thiol-containing molecule according to the present disclosure may be neutral form, or may be a pharmaceutically acceptable salt thereof. For example, in certain embodiments as otherwise described herein, the thiol-containing molecule may be a salt or ester or derivative. Examples of suitable salts include those formed with organic or inorganic acid, such as salts of acetate, tartrate, bitartrate, trifluoroacetate, lactate, maleate, fumarate, citrate, methanesulfonate, sulfate, phosphate, nitrate, or chloride. In particular embodiments, the thiol-containing molecule is a bitartrate salt. For example, in particular embodiments, the cysteamine is cysteamine bitartrate.

The thiol-containing molecule described herein may be administered orally or intraveneously in dosage unit formulations containing conventional non-toxic pharmaceutically acceptable carriers, adjuvants and vehicles. The pharmaceutical compositions described herein may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques, for example with an enteric coating. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

The methods of the present disclosure involve the administration of an effective dose of a thiol-containing molecule to treat IgA nephropathy in mammals such as humans. In certain embodiments as otherwise described herein, the thiol-containing molecule can be administered in a daily amount ranging 0.1 mg/kg to 400 mg/kg, or 1 mg/kg to 400 mg/kg. For example, in certain embodiments, the thiol-containing molecule can be administered in daily amount ranging from 5 mg/kg to 80 mg/kg. In other embodiments, the thiol-containing molecule can be administered in a daily amount ranging from 10 mg/kg to 250 mg/kg, or 20 mg/kg to 250 mg/kg, or 40 mg/kg to 250 mg/kg. For example, in particular embodiments, the thiol-containing molecule is cysteamine or N-acetylcysteine, and is administered in a daily amount in the range of 1 mg/kg to 150 mg/kg, for example, in the range of 2 mg/kg to 100 mg/kg, or 5 mg/kg to 80 mg/kg, or 5 mg/kg to 60 mg/kg, or 10 mg/kg to 50 mg/kg. It is to be understood that the milligram dosage quoted reflects the equivalent milligrams of pure thiol-containing compound (i.e., without inclusion of any anions or salts in the molecular weight).

In certain embodiments as otherwise described herein, the dose of the thiol-containing molecule can be administered one or more times per day, such as one time per day, two times per day, three, four, or six times per day. In certain embodiments as otherwise described herein, the thiol-containing molecule or the composition comprising the thiol-containing molecule is administered for any suitable period of time. For example, the thiol-containing molecule or the composition comprising the thiol-containing molecule may be administered for a period of at least three weeks, or a period of 4-6 weeks, or for a period of at least 4 weeks, 6 weeks, 8 weeks, 12 weeks, or at least 24 weeks.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

EXAMPLES

Methods

Recombinant Construction of Rat and Human IgA Mimetics

DNA sequence (SEQ ID NO.:1) that encodes wild-type rat IgA-Fc segment of CH2-CH3-TP (SEQ ID NO.:2) was cloned into PET30a vector (Invitrogen, Carlsbad, CA) with an N-terminus 6×His-tag using standard procedures. Corresponding point mutations of C471 S (SEQ ID NOs.:3 and 11((rat and human, respectively), C311S (SEQ ID NO.:5) (rat) and C311/471S (SEQ ID NO.:7)(rat) were generated by site-directed mutagenesis using standard procedures. Human IgA1-Fc CH2-CH3-TP cDNA (SEQ ID NO.:9) and its mutant for C471S (SEQ ID NO.:11) were fused to sequences encoding IL-2 signal peptide and 6×His-tag at the 5'-end in pcDNA3 vector (Invitrogen, Carlsbad, CA) using standard procedures. Rat IgA analogs were expressed in BL21 DE3 strain of *E. coil* and recombinant protein were purified from the bacterial lysate using Histrap HP columns (GE Healthcare) by running fast protein liquid chromatography (FPLC). Human recombinant IgA mimetics were produced from human embryo kidney (HEK293) cells by transfection of the pcDNA3 plasmids. Recombinant IgA proteins expressed by the cells were secreted into the culture medium, and they were subsequently purified by Histrap HP columns via running FPLC following standard procedures, such as those discussed in Liu, "Novel ACE2-Fc chimeric fusion provides long-lasting hypertension control and organ protection in mouse models of systemic renin angiotensin system activation." *Kidney Int.* 94(1):114-125 (2018).

Native IgA Purification from Human Serum

IgA1 from IgA nephropathy patient sera was purified by Jacalin (Thermo Scientific, USA)-directed affinity chromatography. Poly-IgA1 contents were further enriched via running Superdex 200 Increase gel filtration molecular sieve (GE Biosciences) and collecting high-molecular weight fractions from an AKTA protein purification system (GE Biosciences). Human serum from healthy donors was purchased from Sigma-Aldrich and total IgA1 was also purified by running Jacalin-directed chromatography. Purified total IgA1 was used for injecting mice.

Analysis of Intermolecular Disulfide Bond Formation in IgA Self-Aggregates: Determination of Poly- and Monomeric IgA Content The overall complex size of IgA aggregates was determined either by size-exclusion chromatography (SEC: Superdex 200 Increase 10/300 by GL Cytiva), or by SDS-PAGE. For evaluating the involvement of intermolecular disulfide connectivity in IgA complexes, IgA samples were treated with either reducing agents, such as DTT, TCEP or reduced glutathione (Sigma), or interventional drugs, such as cysteamine (Sigma), WR-1065 (Sigma) and N-Acetyl-L-cysteine (VWR Chemicals) in phosphate-buffered saline (PBS) pH7.4. Before running on SEC, samples were treated with the drugs at indicated concentrations at 37° C. for one hour.

In the meantime, the SEC column was also equilibrated with PBS supplemented with the reducing agent at the same concentration. For running SEC, 100 μL of the recombinant IgA (concentration varies between 1 mg/mL and 8 mg/mL) or purified native human IgA1 (~1 mg/mL) was loaded to the column and UV absorption was recorded following elution. Recombinant IgA typically formed two elution peaks: a minor peak of ~800 kDa poly-rIgA followed by a major peak of ~170 kDa of monomeric rIgA. The ratios between poly-rIgA and mono-rIgA were calculated as between the corresponding areas under the curve (AUC), and the treatment effect of the thiol agents was judged by the reduction of the poly-rIgA level with a compensatory increase of the mono-rIgA content. With regard to native human IgA1, SEC showed three partially overlapping peaks of poly-, di- and mono-IgA1, and treatment effect was judged by the reduction of the poly-IgA1 level with a compensatory increase of the mono-IgA1 content.

SDS-PAGE and Western Blotting

Proteins in sample buffer (Bio-Rad Laboratories, Hercules, CA, USA) with or without TCEP (for reducing or nonreducing condition, respectively) were resolved by 4-12% SDS-PAGE (Bio-Rad Laboratories). IgA bands were subsequently visualized either by staining with GelCode Blue (Thermo Fisher Scientific), or by Western blotting on PVDF membrane. For Western blotting, 5% non-fat milk was used in blocking for one hour at room temperature. The membrane was then incubated with mouse anti-Histag antibody (Thermo Scientific), or HRP-conjugated goat anti-rat IgA α-chain antibody (Cat. ab97185, Abcam, UK), or goat anti-human IgA HRP antibody (Cat: 2050-05, SouthernBiotech) for detecting rat or human IgA (Fc), respectively. The membrane was developed using the Clarity™ ECL substrate (Bio-Rad Laboratories, CA, USA).

Transmission Electron Microscopy (TEM) Analyses

TEM analyses of the structures of poly-rIgA and mono-rIgA were conducted following a standard negative staining protocol. In brief, purified poly-rIgA or mono-rIgA was diluted in PBS to a concentration of 100 µg/ml. A 10 µl droplet was applied to a glow—discharged carbon-coated copper grid and allowed to sit for 1 min. The grid was washed by dipping in two separate drops in water followed by two drops in 2% uranyl acetate (Electron Microscopy Sciences). Grids were examined at the Northwestern Electron Probe Instrumentation Center (EPIC) using Hitachi HT-7700 Biological S/TEM Microscope.

Cysteamine Treatment of IgA Deposition in Rat and Mouse Model

To establish the passive rat model, 5 mg/kg.BW recombinant rat rIgA, which contained a fraction of poly-rIgA, were i.v. injected daily to six 14-weeks old male Wistar rats (Charles River Labs, USA) for 5 consecutive days. Every day, three rats in each group had received a subcutaneous dose of either 250 mg/kg cysteamine, or buffer control, two hours before the rIgA injection. Twenty-four hours after the last injection of rIgA, kidneys were collected for immunofluorescence detection of deposits with goat-anti-rat IgA antibody (Cat: STAR111, Biorad laboratory). Similarly, a passive IgA nephrophathy mouse model was established by injecting 35 mg/kg purified human IgA1 in BALB/c mice (Charles River Labs). Two hours before IgA1 injection, six mice in each experimental group had each received a pre-treatment dose of either 200 mg/kg cysteamine, or PBS, via subcutaneous injection. Two and a half hours after human IgA1 injection, kidneys were harvested, and specimens were stained with FITC-conjugated anti-human IgA antibody (Cat: 2050-02, SouthernBiotech). Plasma samples were collected at 0.5 h, 1 h and 2 h after IgA1 injection of all mice.

Immunofluorescence Staining

Frozen tissues were sectioned at 4 µm for IgA detection using goat anti-rat IgA (Cat: STAR111, Bio-Rad Laboratories) at 1:100, or anti-human IgA antibody (Cat: 2050-02, Bio-Rad Laboratories) at 1:80 dilution. Anti-collage IV α1 (Cat: NB120-6586, Novus) at 1:500 dilution, rat anti-mouse CD31 (Cat: 553370, BD Biosciences) at 1:100 dilution and DAPI were used as counterstaining. Immunofluorescence images were captured by Nikon Ti2 Widefield microscope. The mean immunofluorescence intensity per glomerulus area was derived from 15 glomeruli per kidney section assisted by Image J software.

Statistical Analyses

Data are displayed graphically, and statistical analyses were performed using GraphPad Prism 5.0 (GraphPad Software). Group data are reported as mean±SEM. Significance between two groups was determined by t-test. Significance was accepted when p-values were ≤0.05.

Example 1

Figure 7:
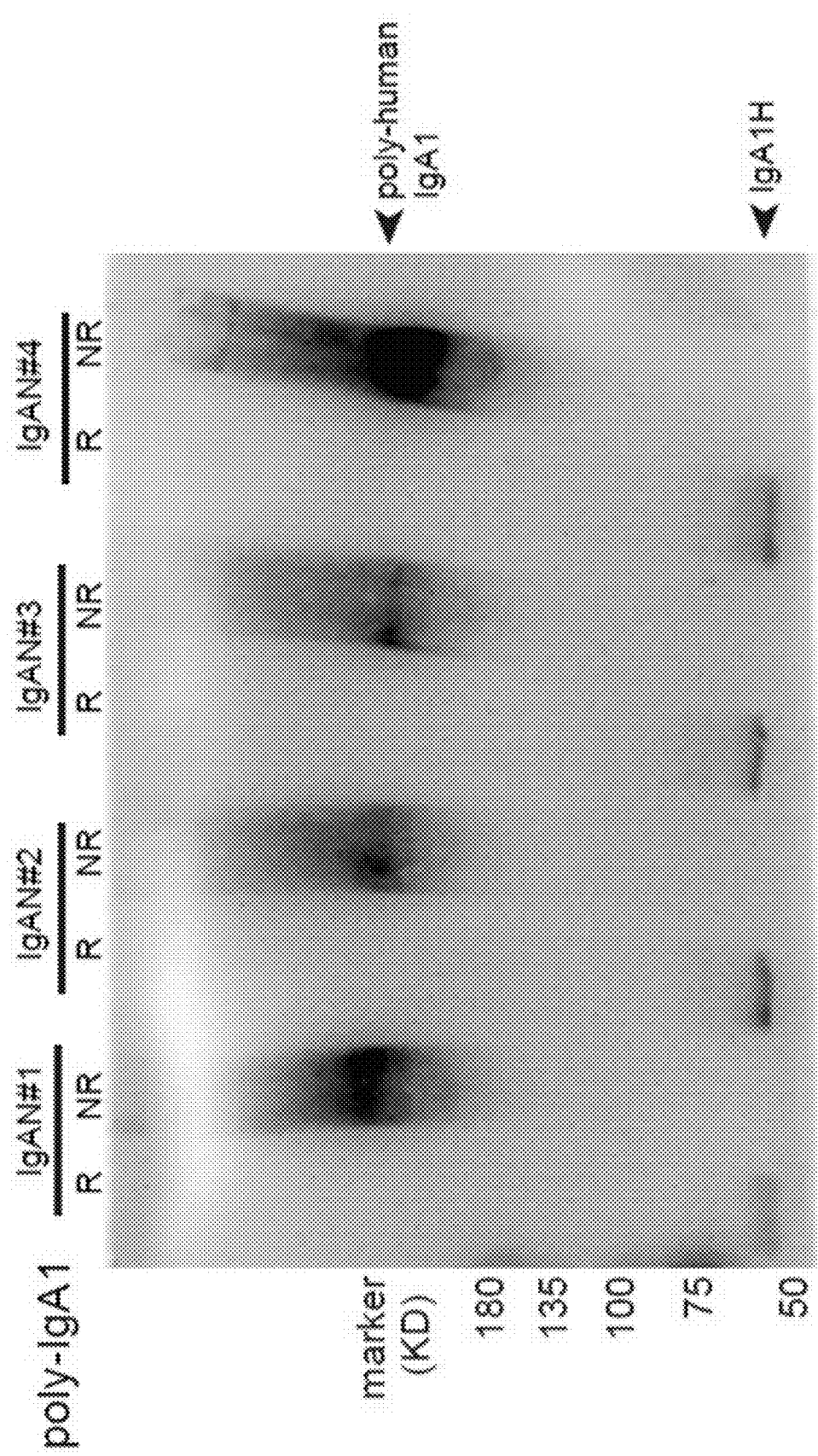
FIG. 7: Individual IgA nephropathy patients' poly-IgA complexes disassembled by reducing agent. Plasma samples were collected from eight IgA nephropathy patients. Following purification of total IgA1 by Jacalin beads, poly-IgA1 complexes were extracted by SEC. Purified complexes were treated in the presence or absence of 2-mercaptoethanol and were then resolved by SDS PAGE and probed by anti-IgA Western blotting. In all samples, with the absence of 2-mercaptoethanol (NR), poly-IgA1 appeared at ~600 kDa. With 2-mercaptoethanol (R), a single ~65 kDa IgA1 band corresponding to IgA1 heavy chain was observed for each sample.
Figure 7:
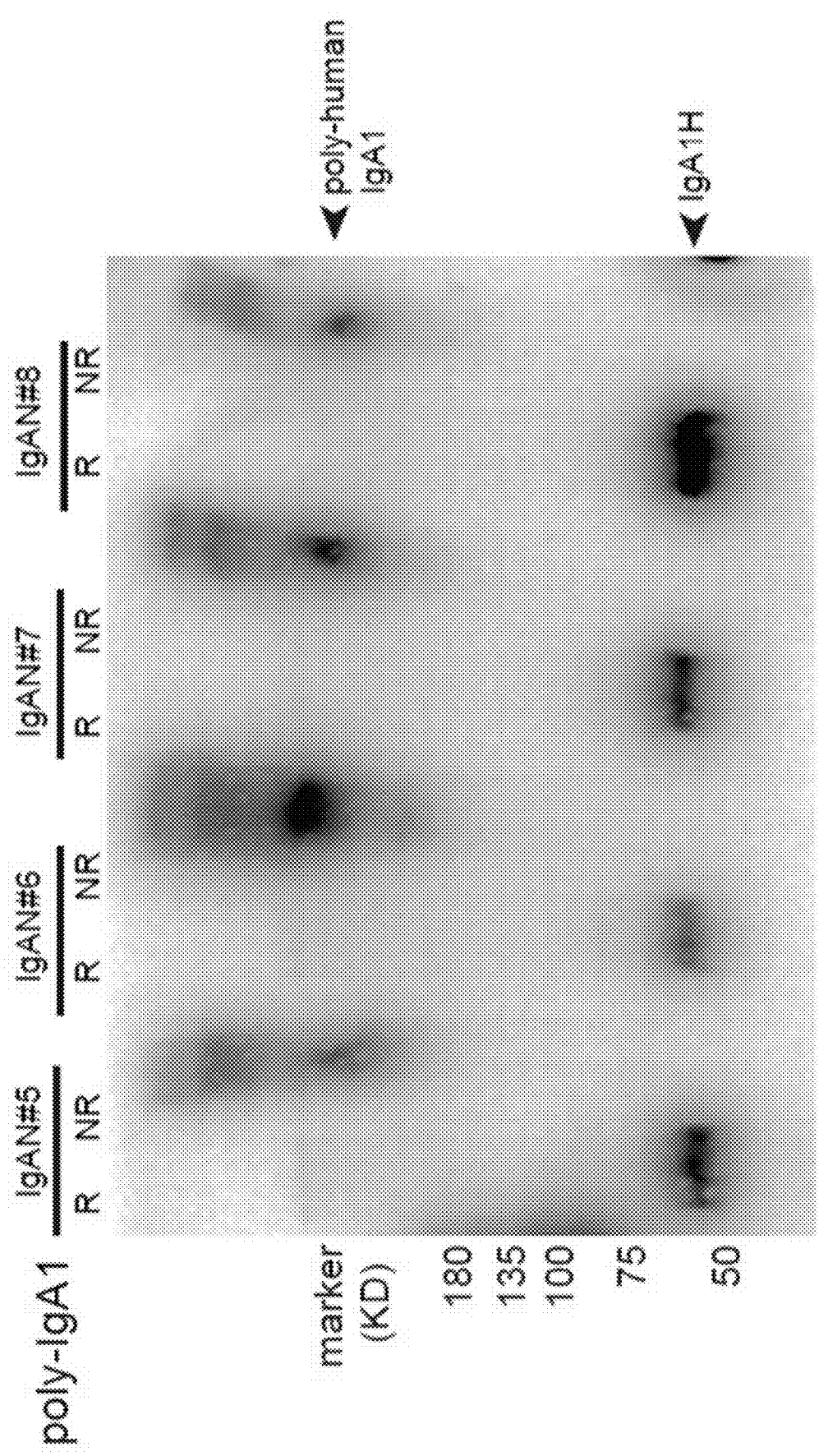

High Molecular Weight IgA Complexes Extracted from IgA Nephropathy Patients' Plasma Contain Intermolecular Disulfide Connections In this Example, it was sought to isolate high molecular weight IgA complexes, such as poly-IgA, from plasma of IgA nephropathy patients. A standard workflow was followed to purify total IgA1 from pooled plasma using a jacalin-conjugated affinity column, and then subjected the extraction to size-exclusion chromatography (SEC). IgA monomers formed the dominant peak of ~160 kDa, preceded by dimeric sIgA of ~350 kDa (FIG. 1, part A). Further ahead, poly-IgA formed additional overlapping minor peaks at >670 kDa (FIG. 1, part A). By running SDS-PAGE of the poly-IgA fraction under both reducing and nonreducing conditions, it was determined that the molecular complexes of IgA were connected through disulfide bridges (FIG. 1, part B). To be certain of broad presence reduction-sensitive IgA complexes, another cohort of patients was recruited. IgA1 complexes were extracted from individual patients by SEC and analyzed the contents by SDS-PAGE. These samples showed varying levels of high molecular weight IgA1 contents that could be dissociated by reducing agents (FIG. 7).

Example 2

Figure 2:
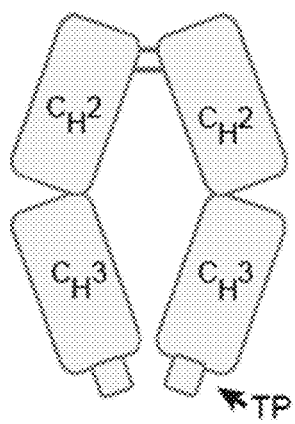
FIG. 2: Intermolecular disulfide bond(s) involved in the self-aggregation of recombinant poly-rIgA. A. Recombinant human and rat IgA mimetics are comprised of the CH2-CH3-Tailpiece (TP) segment of IgA heavy chain (Left). Like native IgA heavy chain, the mimetics form a duplex that is referred to as mono-rIgA. Transmission electron miscroscopy (TEM) images confirmed rat rIgA duplexes in donut-like appearances (right). B. Rat rIgA was resolved by size-exclusion chromatography (SEC) with a clear separation of its poly- and mono-rIgA contents. C. SDS-PAGE results confirmed the presence of disulfide connections among self-associated rIgA in poly-rIgA complexes (NR: non-reducing condition): Under reducing condition (R) both poly- and mono-rIgA reduced to single chains of 32 kDa. D. TEM images of poly-rIgA SEC fraction showed rIgA aggregates (left: arrowheads): High magnification images (middle panels) show structures with multiple circular voids of monomeric rIgA units, in contrast to mono-IgA that all appeared as single donut-like structures (arrowheads). Scale bar: 10 nm.
Figure 2:
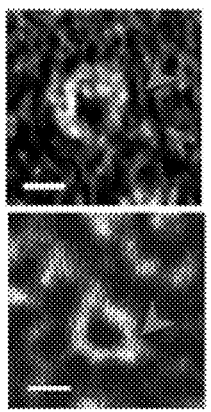
Figure 2:
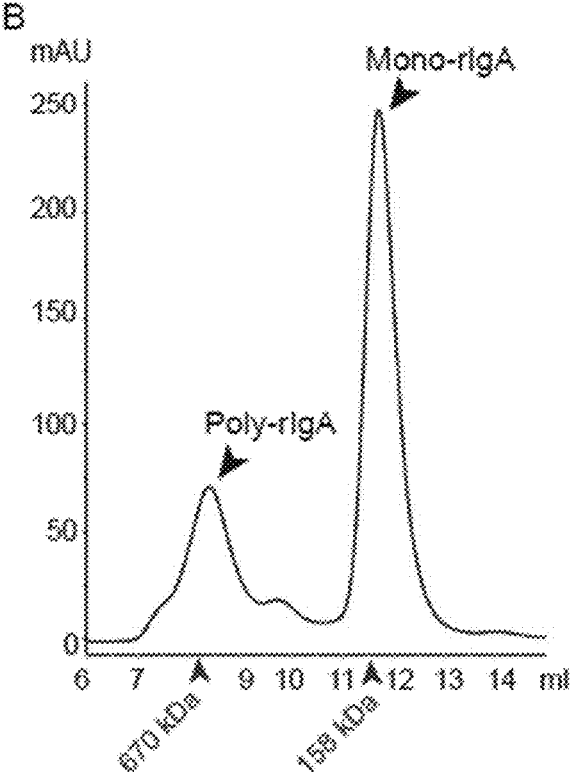
Figure 2:
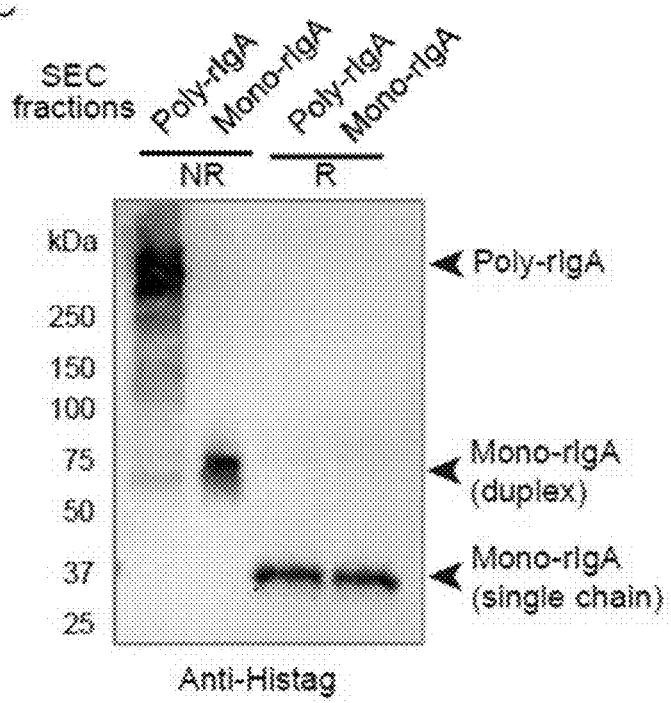
Figure 2:
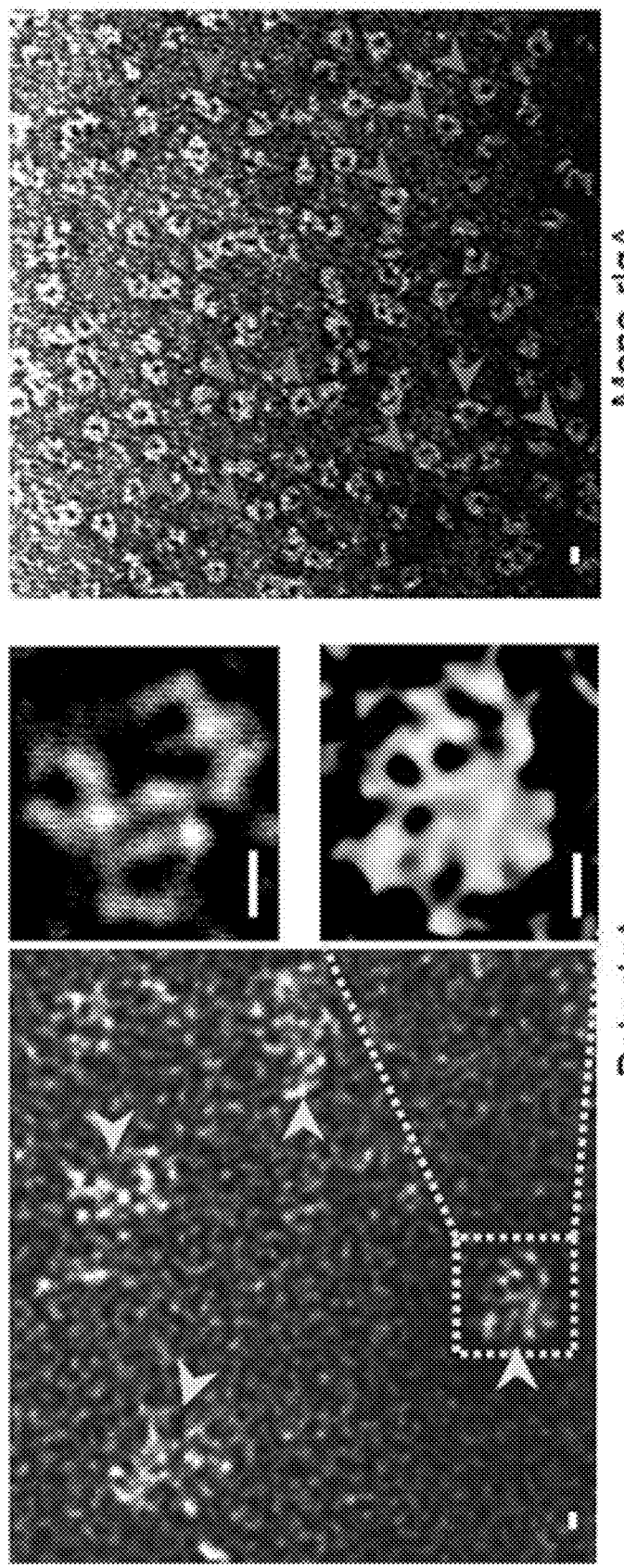
Figure 3:
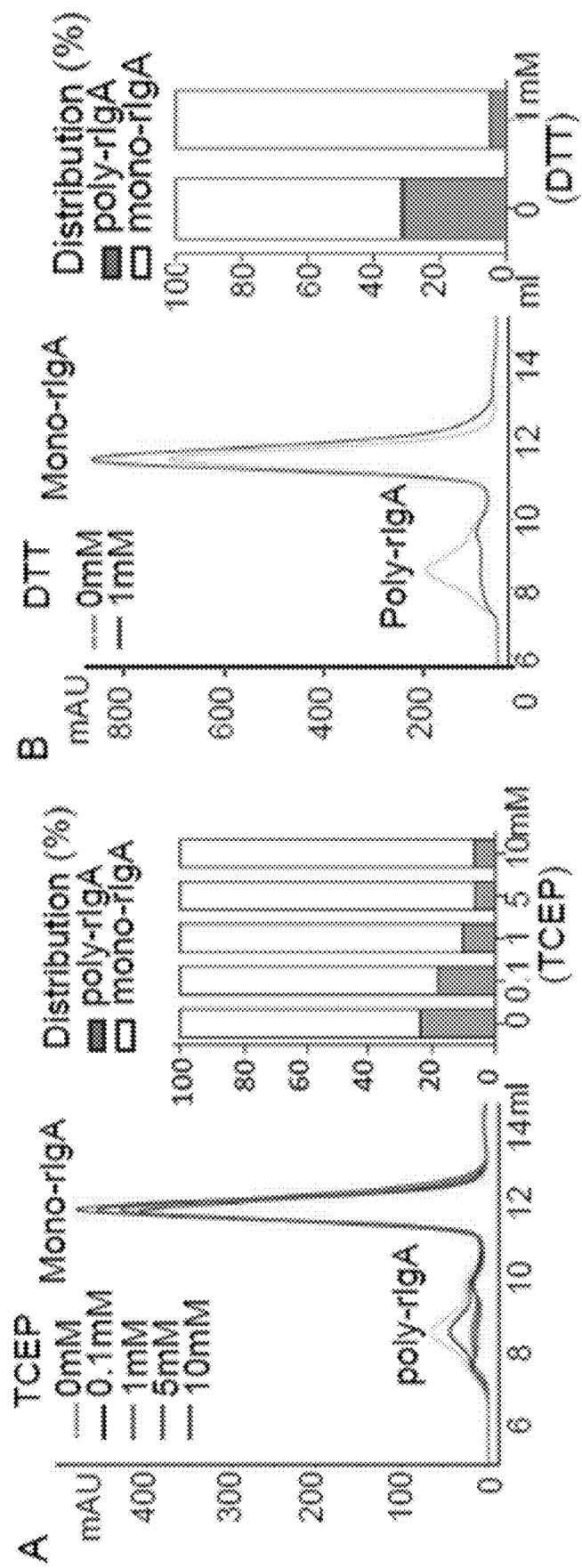
FIG. 3: Mutagenesis analyses of cysteine-311 and cysteine-471 regarding formation of intermolecular disulfide bond. A-C. SEC analyses of rIgA in the presence of reducing agents of TCEP, dithioreitol (DTT) or glutathione, respectively. D-F. SEC tracing of C471S, C311/471S, and C311 mutations of rIgA as compared to wild-type, respectively. The bar graphs show quantitation of poly- vs. mono-rIgA contents based on area under the curve (AUC). G. Comparing HEK293 cell-produced human rIgA (hu-rIgA) wild-type and C471S mutant in terms of their poly-hu-rIgA contents as revealed by SEC.
Figure 3:
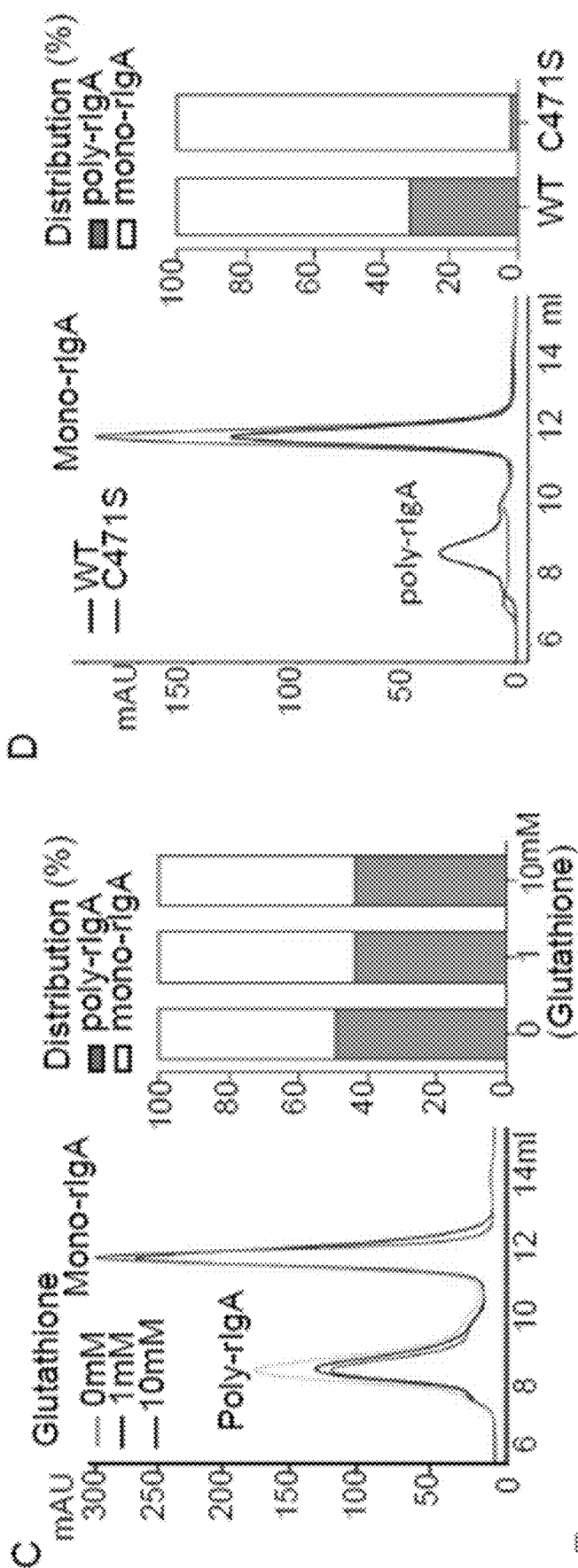
Figure 3:
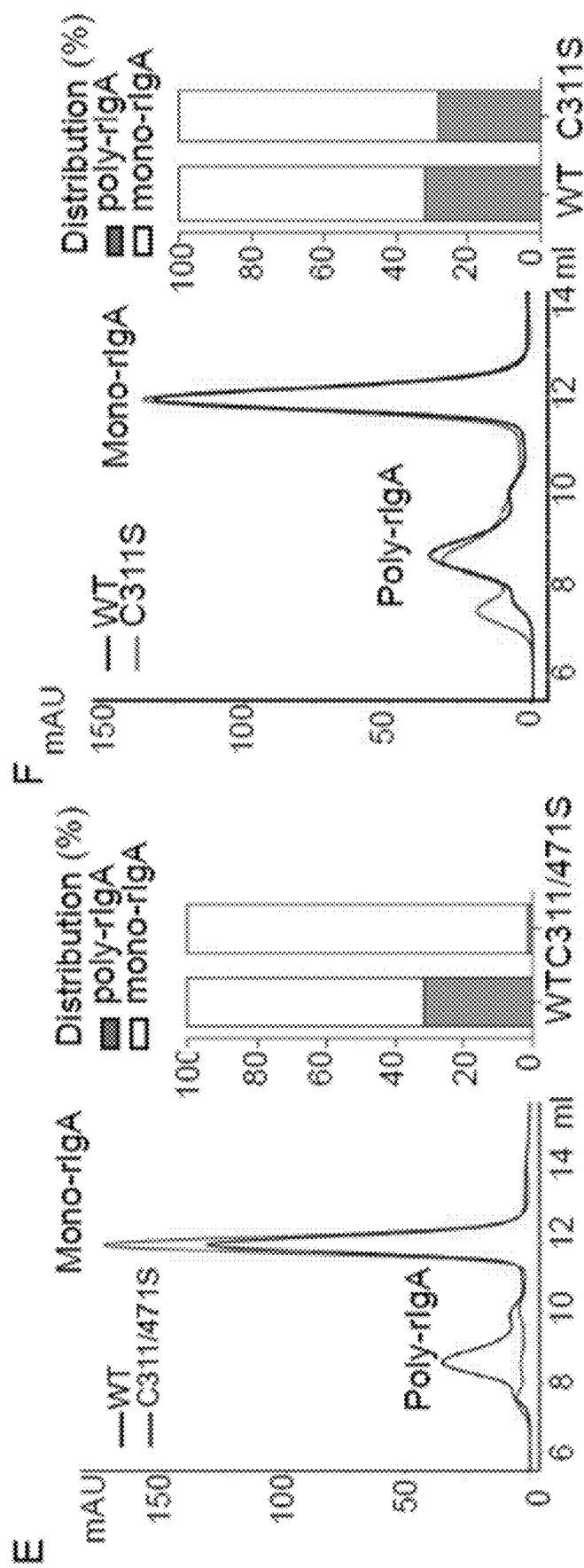
Figure 3:
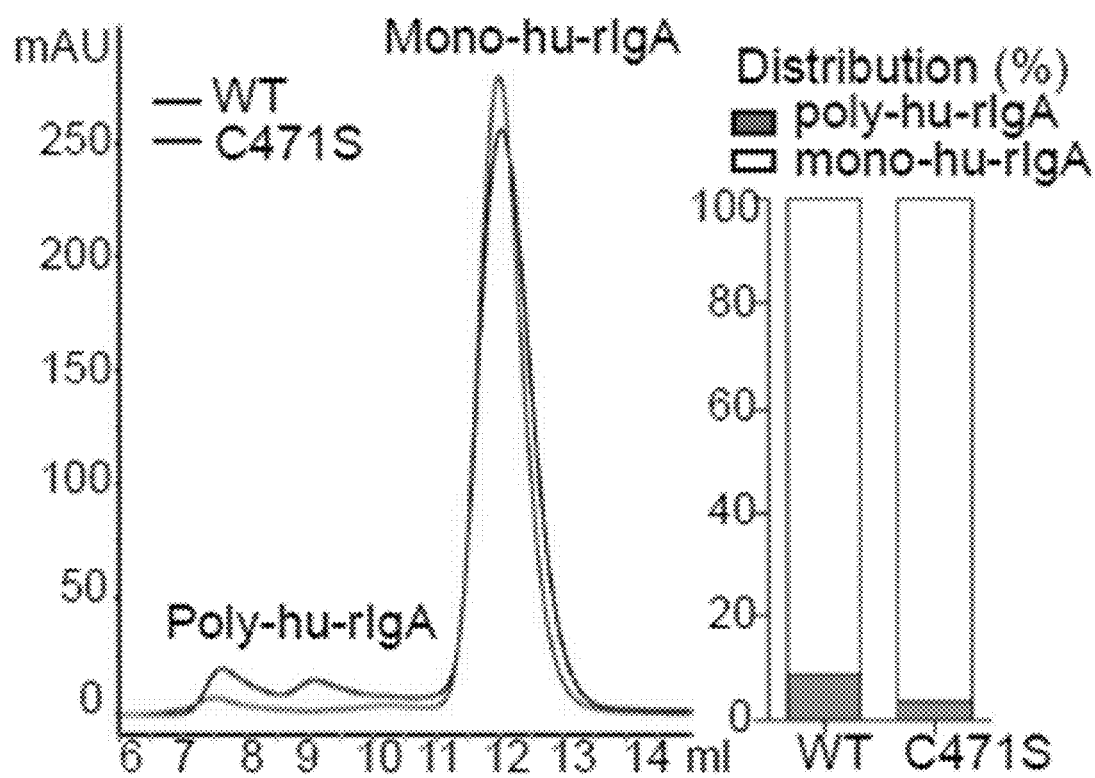

Mutagenesis of Recombinant IgA Mimetics Identified Penultimate Residue Cysteine-471 in Promoting IgA Aggregation To further investigate specific cysteine residue(s) involved in IgA complexes, expression vectors were constructed to produce recombinant IgA (rIgA) Fc segments of rat and human sequences (FIG. 2, part A) as discussed above. Rat IgA analogs were expressed in BL21 DE3 strain of *E. coil* and recombinant protein were purified from the bacterial lysate using Histrap HP columns (GE Healthcare) by running fast protein liquid chromatography (FPLC). Human recombinant IgA mimetics were produced from human embryo kidney (HEK293) cells by transfection of the expressing plasmids. Recombinant IgA proteins expressed by the cells were secreted into the culture medium, and they were subsequently purified by Histrap HP columns by FPLC using standard procedures. Like native IgA heavy chain, these single-chain rIgAs also folded into duplex, referred to as mono-rIgA in keeping with tradition. Rat rIgA was produced from bacterial expression as discussed above. Rat rIgA was resolved by SEC (FIG. 2, part B), showing a major peak of mono-rIgA duplex at ~64 kDa, preceded by a minor peak of poly-rIgA at >500 kDa. SDS-PAGE results further confirmed intermolecular disulfides in connecting rIgA units (FIG. 2, part C). Transmission electron microscopy (TEM) showed interconnected rIgA structures in high-order complexes (FIG. 2, part D). To further demonstrate that poly-rIgA was also linked by disulfide bridges, reducing agents were added such as Tris(2-carboxyethyl)phosphine hydrochloride (TCEP), 1,4-Dithiothreitol (DTT) or glutathione to rIgA. Analyses on SEC showed poly-rIgA disassembled into monomers by TCEP and DDT, and to a lesser degree, by glutathione (FIG. 3, part A-3, part C). Specifically, SEC analyses showed a concentration-dependent reduction of the high molecular weight poly-rIgA peak by TCEP. Meanwhile, there was a slight compensatory increase of the mono-rIgA content (FIG. 3, part A), as expected.

Considering that the fragment contained Cys311 and Cys471 that, in the absence of J-chain and SC, were in their free forms and available for connecting other rIgA units, mutagenesis studies were conducted of these two cysteines. Cys311 and Cys471 were either individually, or together, mutated to serine (S) as discussed above. These C311S (SEQ ID NO.:6) (rat only) and C471S single mutants (SEQ ID NOS.: 4 AND 12) (rat and human, respectively), and C311/471S double mutant (SEQ ID NO.:8) (rat only) were produced as rat rIgA proteins. By examining the SEC traces of these mutants, it was noticed that, while the monomers of all variants appeared the same, there were dramatic differences in the poly-rIgA contents. Notably, the prominent high molecular weight peak for poly-rIgA completely disappeared in C471S single mutant and in C331/471S double mutant (FIG. 3, part D-3, part E). Meanwhile, C311S-alone still had poly-rIgA contents, albeit eluted at a different time in SEC than the wild-type protein (FIG. 3, part F). In addition, SDS-PAGE results further confirmed Cys471's involvement in poly-rIgA formation.

In parallel, the experiments were repeated using human rIgA1-Fc (SEQ ID NO.:10) and its C471S mutant (SEQ ID NO.:12), which were produced from mammalian cell expression. Wild-type rIgA1 also had both monomer and polymer contents, in contrast to C471 S showing greatly reduced level of poly-rIgA1 (FIG. 3, part G), suggesting that Cys471 promotes rIgA self-association.

Example 3

Cysteamine Reduces Poly-IgA Levels In Vitro

Figure 4:
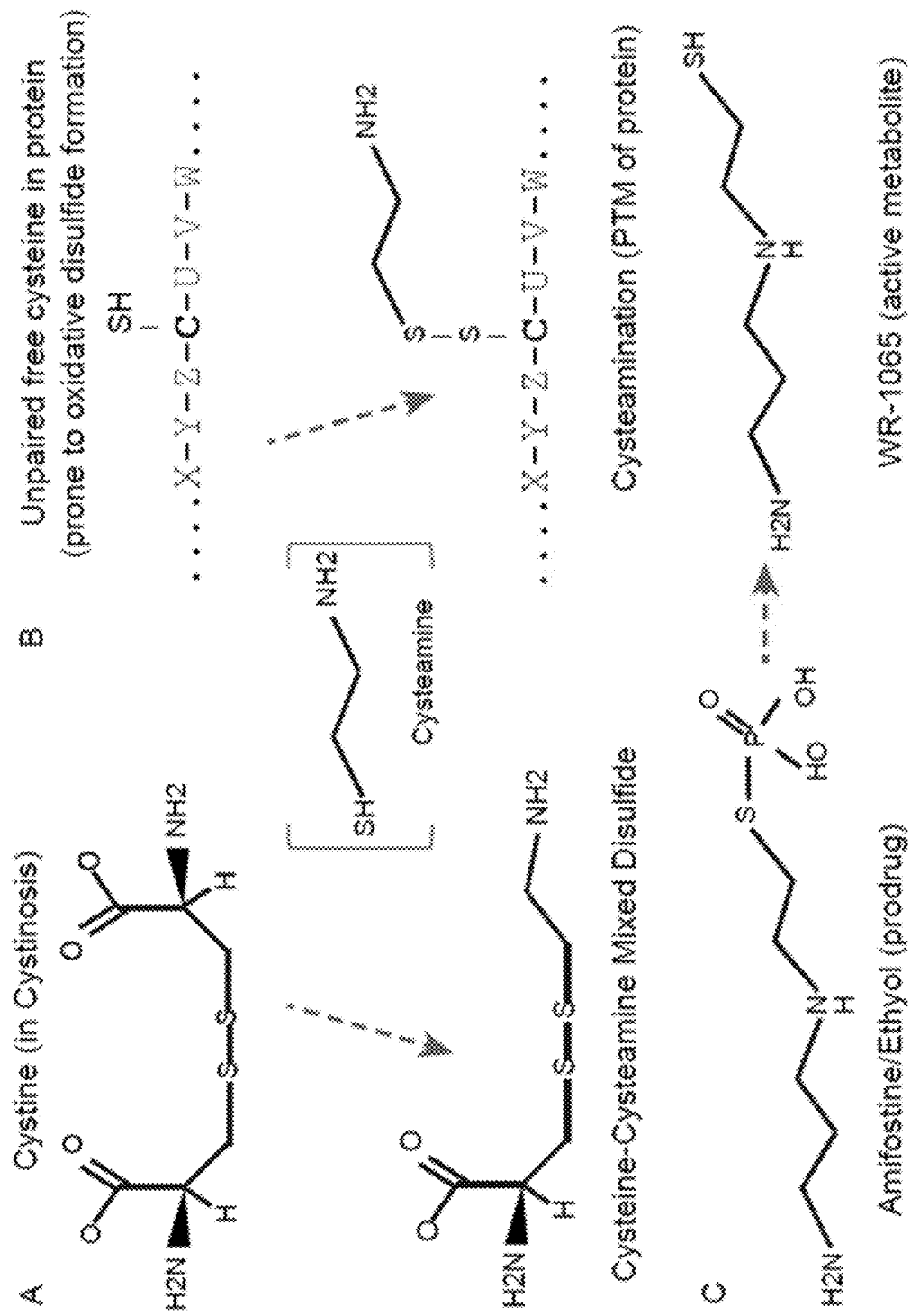
FIG. 4: Cysteamine reacts with amino acid cysteine or free cysteine in protein. A. Drug action of cysteamine in treatment of cystine crystals in cystinosis via formation of cysteine-cysteamine (soluble) mixed disulfide. B. Both human cell-produced endogenous cysteamine and cysteamine drug interact with susceptible cysteine residues in proteins, such as Cys471 in human IgA1, as a form of post-translational modification (PTM). C. Another aminothiol drug amifostine (brand: Ethyol) is a prodrug with its active metabolite WR-1065 capable of interacting with small thiol molecules as well as unpaired cysteine residues in proteins.
Figure 5:
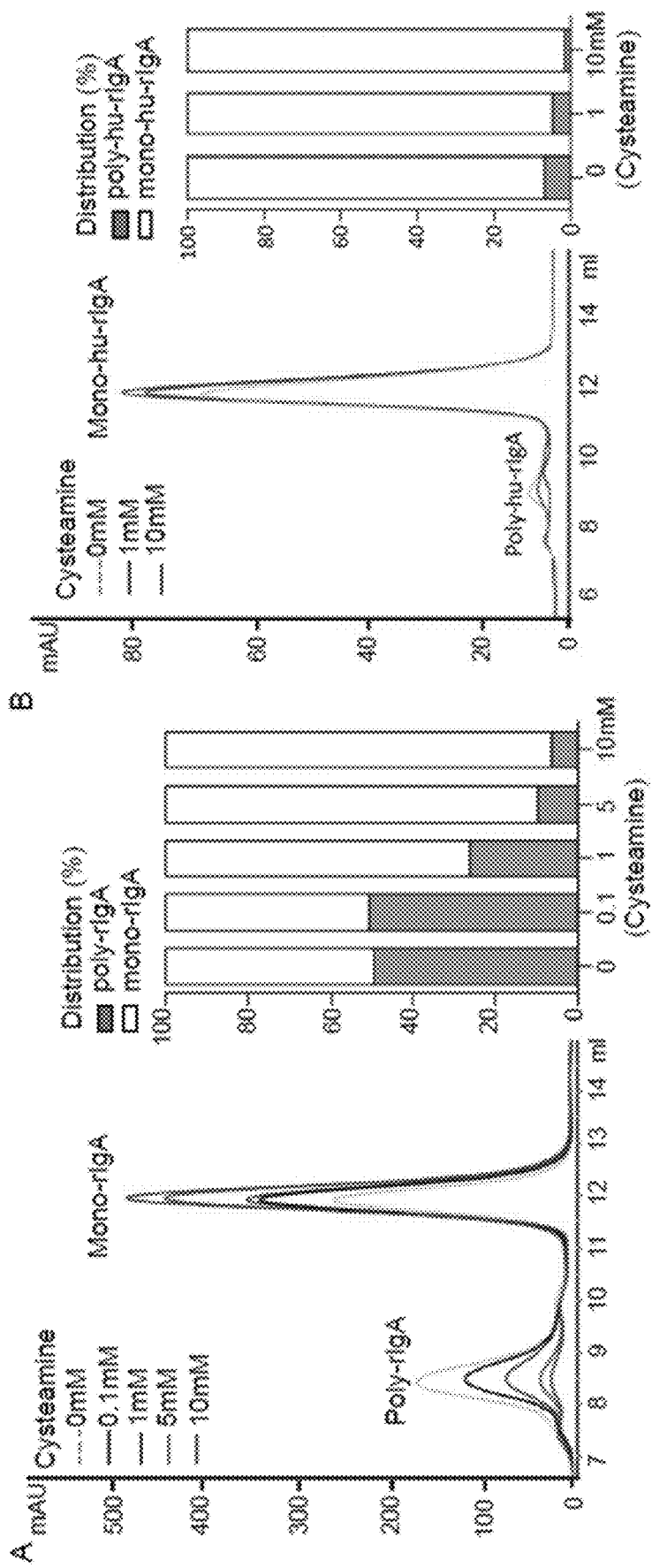
FIG. 5: Cysteamine treatment of either recombinant rIgA or native human IgA ex vivo lowers poly-IgA contents. A. Cysteamine treatment of rat rIgA (produced by *E. coli*) showed greatly reduced poly-rIgA peak in SEC tracing. B. Human recombinant rIgA (hu-rIgA) produced by HEK293 cells has a lower level of poly-rIgA as compared to A. Treatment with cysteamine further lowered the poly-rIgA peak in SEC tracing. C. Using total IgA1 extracted from IgA nephropathy patients, ex vivo treatment with cysteamine also lowered poly-IgA1 levels. D. SDS PAGE analyses showed dose-dependent response of poly-rIgA reduction by cysteamine. Still, the reactions produced duplex mono-rIgA with two rIgA chains remained connected. In contrast, TCEP completely separated paired rIgA heavy chains and resulted in single chain rIgA-Fc. E. and F. In a dose-dependent manner, two additional aminothiol drugs, WR-1065 (E.) and N-acetylcysteine (NAC) (F.) also lowered the level of native human poly-IgA1 contents ex vivo as shown by SEC.
Figure 5:
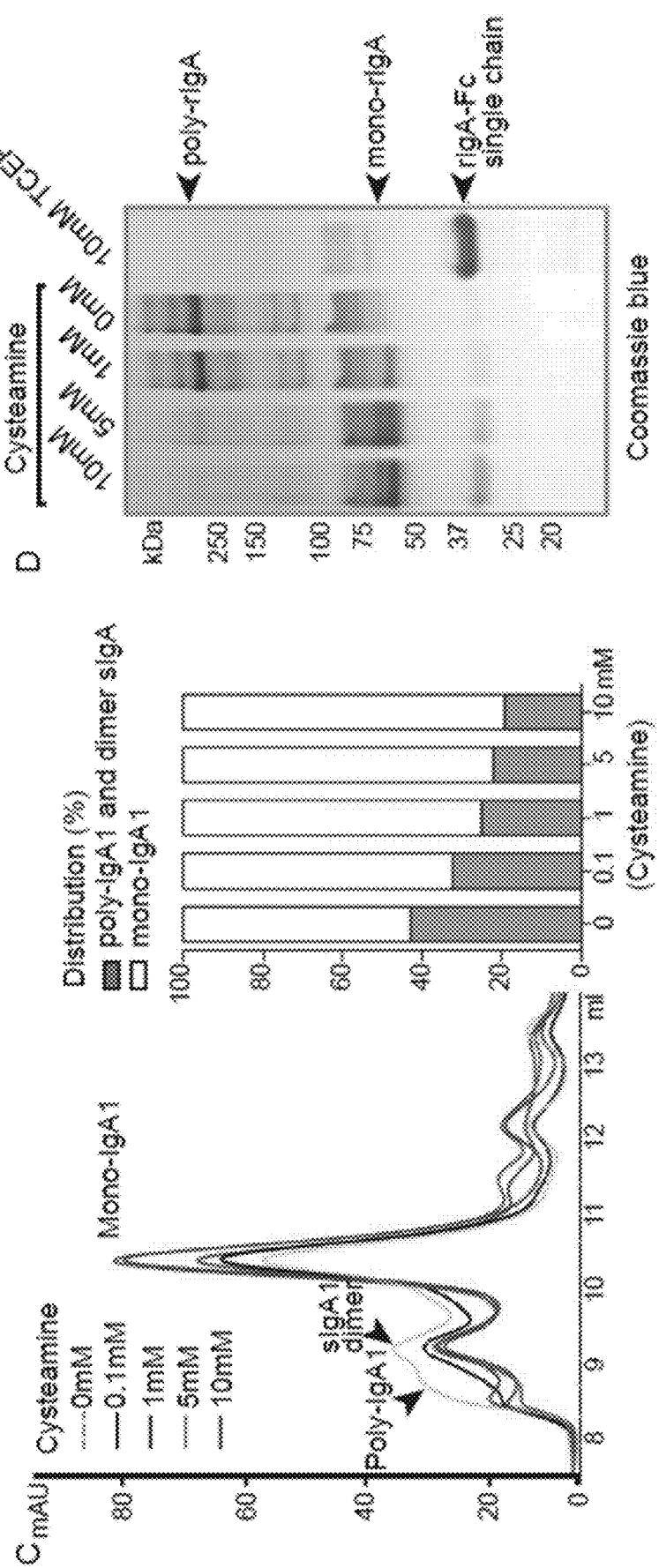
Figure 5:
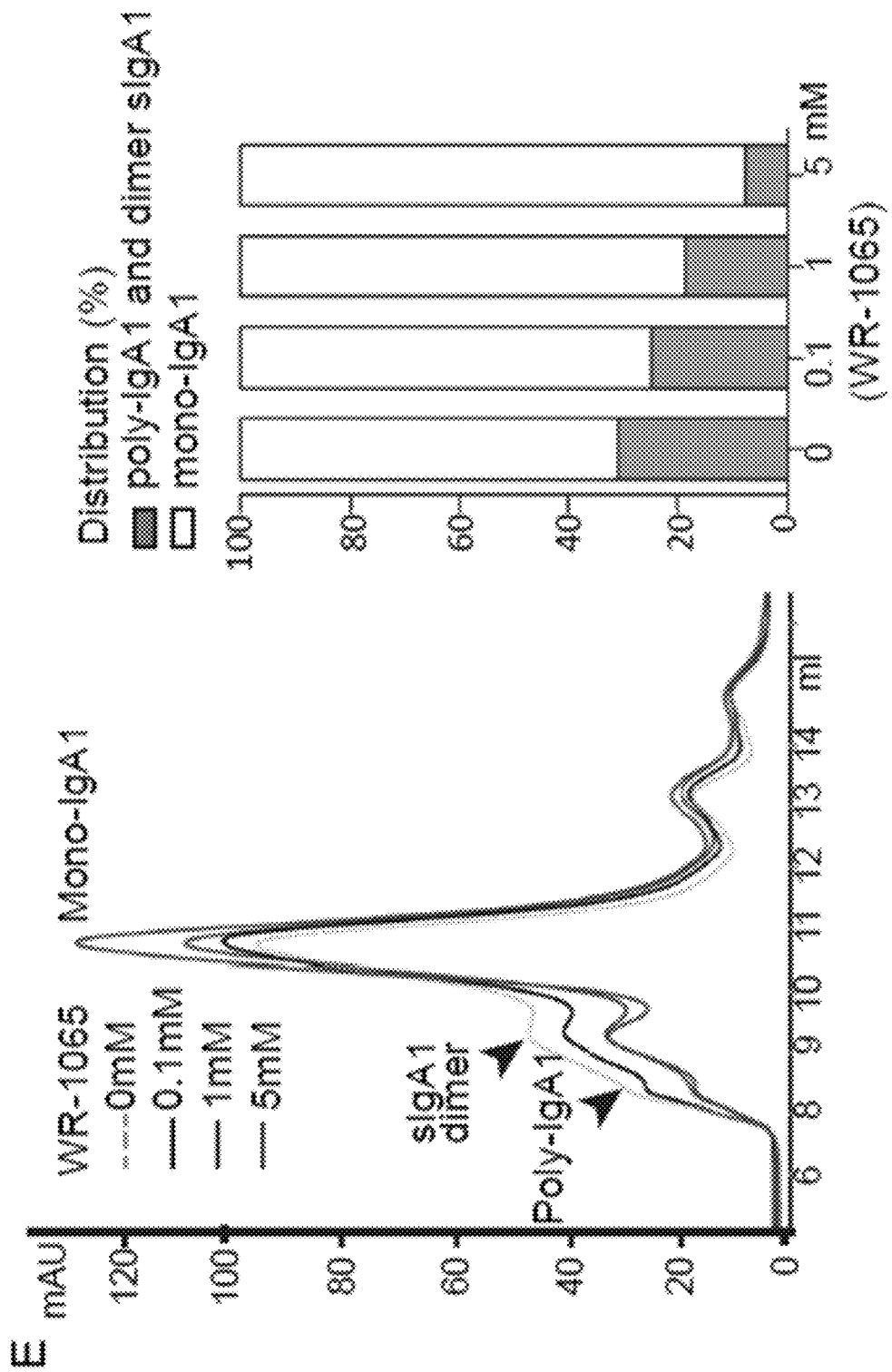
Figure 5:
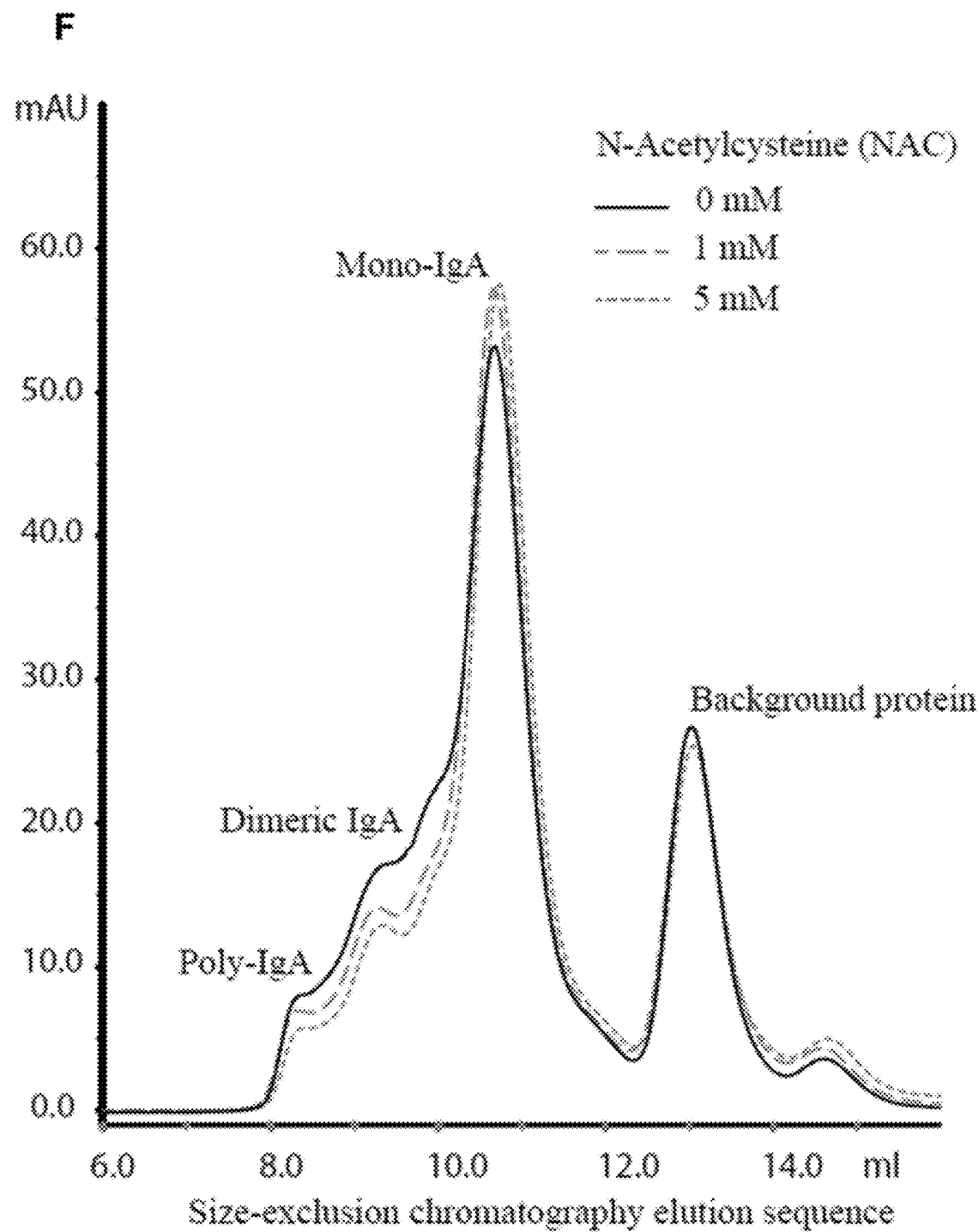

After identifying the tailpiece cysteine in connecting IgA molecules to form aggregates due to spontaneous self-association, it was sought to test interventional drugs to disassemble IgA complexes by reducing the disulfide bond on Cys471. Cysteamine (Cy), an aminothiol that can react with cysteine, is both a natural metabolite produced in mammalian cells and a clinical drug used for treatment of cystinosis. In cystinosis, cysteamine reduces the disulfide bond in cystine, which is the oxidated dimer of amino acid cysteine (FIG. 4, part A). In the context of cysteine residues in proteins, endogenous cysteamine as well as the therapeutic drug forms mixed disulfides with susceptible cysteine sulfhydryl groups in a process called cysteamination (FIG. 4, part B). It was sought to determine whether cysteamine could reduce Cys471-disulfides to disaggregate poly-IgA. Rat rIgA (SEQ ID NO.4) was treated with various concentrations of cysteamine for one hour at 37° C. in phosphate buffered saline at neutral pH and the protein complexes were analyzed by SEC. The SEC column (model: Superdex 200 Increase 10/300 GL by Cytiva) was preequilibrated with the same buffer supplemented with the same concentration of cysteamine. 100 μL of treated rIgA was loaded to the SEC column and the run used the same phosphate buffered saline with corresponding concentration of cysteamine. As expected, the drug effectively lowered poly-rIgA levels in a dose-dependent manner, whereas the relative amounts of mono-rIgA slightly increased (FIG. 5, part A). The result suggested that cysteamine was able to disassemble high molecular weight IgA complexes by disrupting intermolecular disulfide bond. The results are summarized in Table 1:

TABLE 1

| Cysteamine Dosage (mM) | Poly-IgA (%) | Mono-IgA (%) |
| --- | --- | --- |
| 0 | 24.03735 | 75.96265 |
| 0.1 | 18.15234 | 81.84766 |
| 1 | 10.42591 | 89.57409 |
| 5 | 6.413787 | 93.58621 |
| 10 | 6.75919 | 93.24081 |

Human rIgA1 (SEQ ID NO.:10) produced from mammalian expression as discussed above had a smaller fraction of poly-rIgA contents as compared to E. coli produced rat rIgA (compare FIG. 3, part G and 2, part B). Nevertheless, treatment of human rIgA with cysteamine also showed reduction of poly-rIgA levels (FIG. 5, part B). In addition, human IgA1 whole molecule was purified from pooled plasma of IgA nephropathy patients and subjected the sample to different concentrations of cysteamine (FIG. 5, part C). In a dose-dependent manner, cysteamine reduced the amounts of poly-IgA1, whereas the mono-IgA1 levels slightly increased in response to cysteamine, as expected. Because the dimeric sIgA1 peak partially overlapped with that of poly-IgA1 on SEC, it is difficult to accurately assess the impact of treatment to sIgA1 dimers. However, as the overall shape of sIgA peak remained largely unchanged, it was expected that the contents of sIgA1 remained stable. Collectively, these results indicated the structural susceptibility of Cys471 to cysteamine in poly-IgA1, in contrast to the stability of monomers.

To further ascertain the mechanism-of-action of cysteamine in targeting disulfides, nonreducing SDS-PAGE analysis was performed of rat poly-rIgA (FIG. 5, part D). The samples were pretreated with 0 to 10 mM cysteamine, or 10 mM TCEP as positive control. As expected, poly-IgA appeared as >250 kDa bands on SDS-PAGE. Dose-dependent response of poly-rIgA to cysteamine was evident, with majority of the protein running at ~64 kDa of disaggregated monomers. Meanwhile, 10 mM TCEP treatment resulted in further reduction of the molecular weight to ~32 kDa as a single-chain protein, indicating normal disulfide bridges between IgA heavy chains being disrupted. These results suggested that modest reduction activity of cysteamine, as compared to TCEP, was effective in reducing vulnerable intermolecular disulfides between poly-IgA units, while leaving normal disulfides between paired IgA heavy chains intact.

Example 4

WR-1065, the Active Metabolite of Radioprotective Drug Amifostine/Ethiofos (Ethyol), Reduces Poly-IgA Levels Ex Vivo Another thiol-based drug, amifostine (Brand: Ethyol) (FIG. 4, part C), is a clinical radioprotector and cytotoxic chemo-protector. Its active metabolite WR-1065 is an aminothiol that, like cysteamine, can react with cysteine, as well as detoxify non-protein metabolites. Similarly, WR-1065 was added to reactions with total IgA1 extracted from human sera. As expected, SEC analyses showed reduction of poly-IgA levels following treatment (FIG. 5, part E).

Example 5

N-Acetyl-L-cysteine Also Reduces Poly-IgA Levels Ex Vivo

N-Acetyl-L-cysteine, also known as N-Acetylcysteine (NAC), is a dietary supplement. It is also a medication that is used to treat paracetamol (acetaminophen) overdose, and other diseases. For instance, inhaled N-Acetylcysteine is used for mucolytic therapy by breaking down protein disulfide bonds, and therefore reducing the viscosity of mucus. Similar to amifostine in our ex vivo SEC analyses (FIG. 5, part E), when N-Acetylcysteine was used to treat total IgA1 purified from human sera, it lowered poly-IgA levels in a dose-dependent manner (FIG. 5, part F).

Example 6

Figure 6:
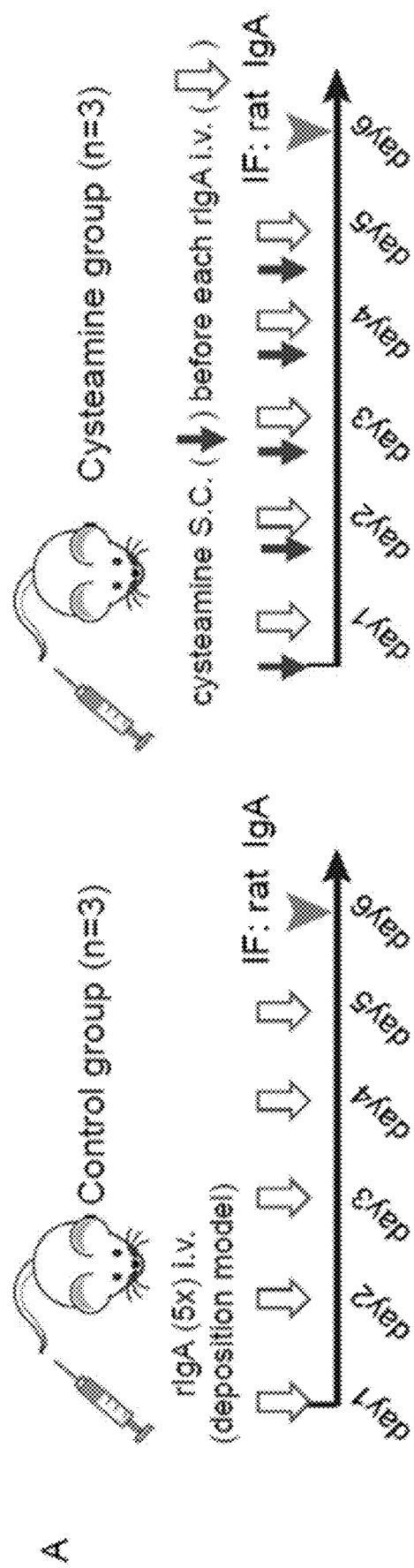
FIG. 6: In vivo treatment of rats and mice with cysteamine lowers IgA deposition in the kidney in injection-induced IgA nephropathy models. A-C. Rat model treated with cysteamine. A. In a rat IgA deposition model, rats received a daily dose of cysteamine, or buffer control, followed by an injection of recombinant rat rIgA for 5 consecutive days. B. Representative immunofluoresence images showed prominent rIgA deposition in glomeruli (Glom: arrowheads) in rats treated with buffer (n=3), in contrast to weaker deposits in cysteamine-treated rats (n=3). C. Quantitation of deposit in glomeruli between control- and cysteamine-treatment groups was compared by t-test (Mean±SEM: 1384±290 vs. 523±76, n=3 in each group). D. Mouse model of IgA deposition from injection of human IgA1 purified from human plasma. Each mouse was injected with a single dose of purified human IgA1 two hours after pretreatment with either cysteamine or buffer control. E. The buffer control group of mice (n=6) had prominent IgA1-deposition in glomeruli (Glom: arrowheads). In contrast, pretreatment of the mice with cysteamine (n=6) greatly reduced IgA1 deposition. F. Quantification of glomerular IgA1 intensity between buffer- and cysteamine-treatment groups (Mean±SEM: 2293±163 vs. 870±193, n=6 in each group). Scale bar: 50 μm.
Figure 6:
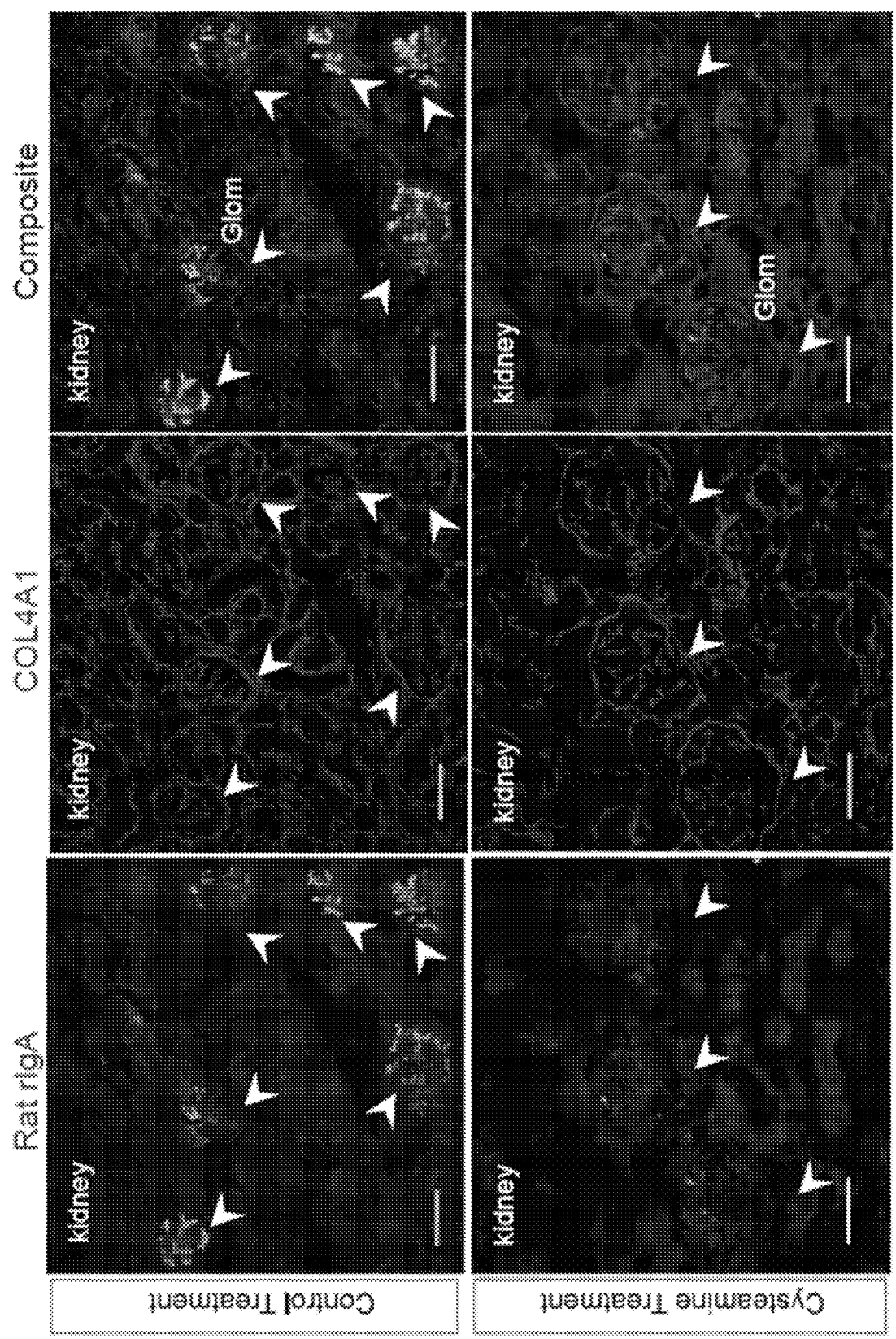
Figure 6:
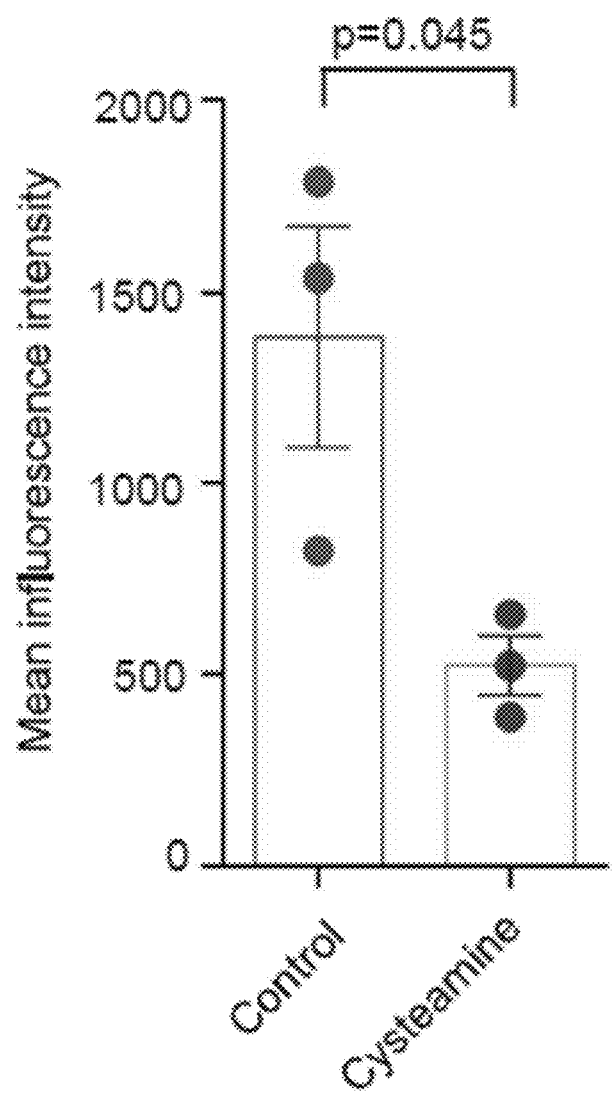
Figure 6:
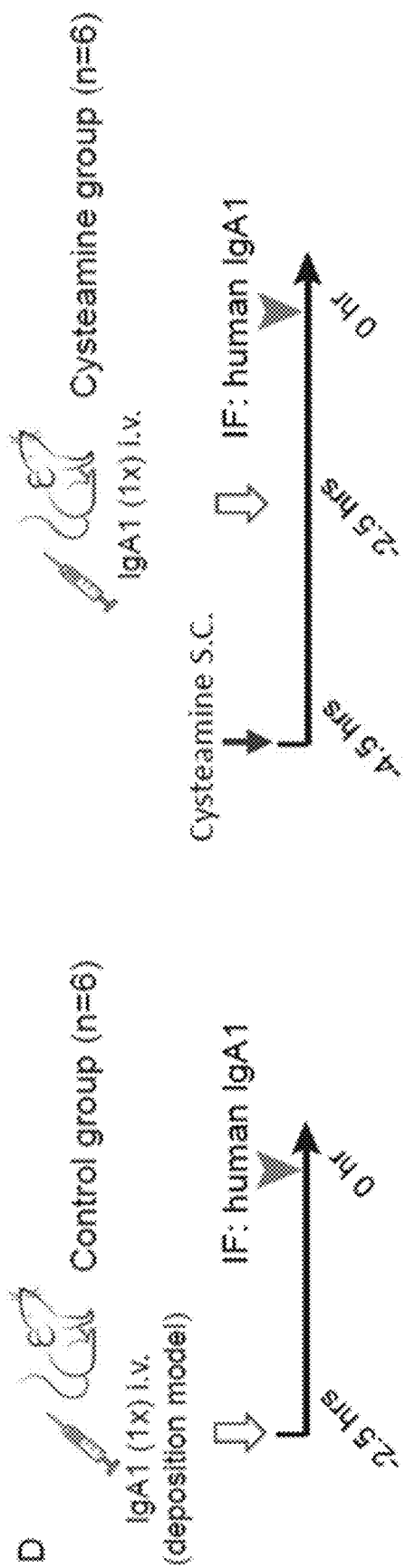
Figure 6:
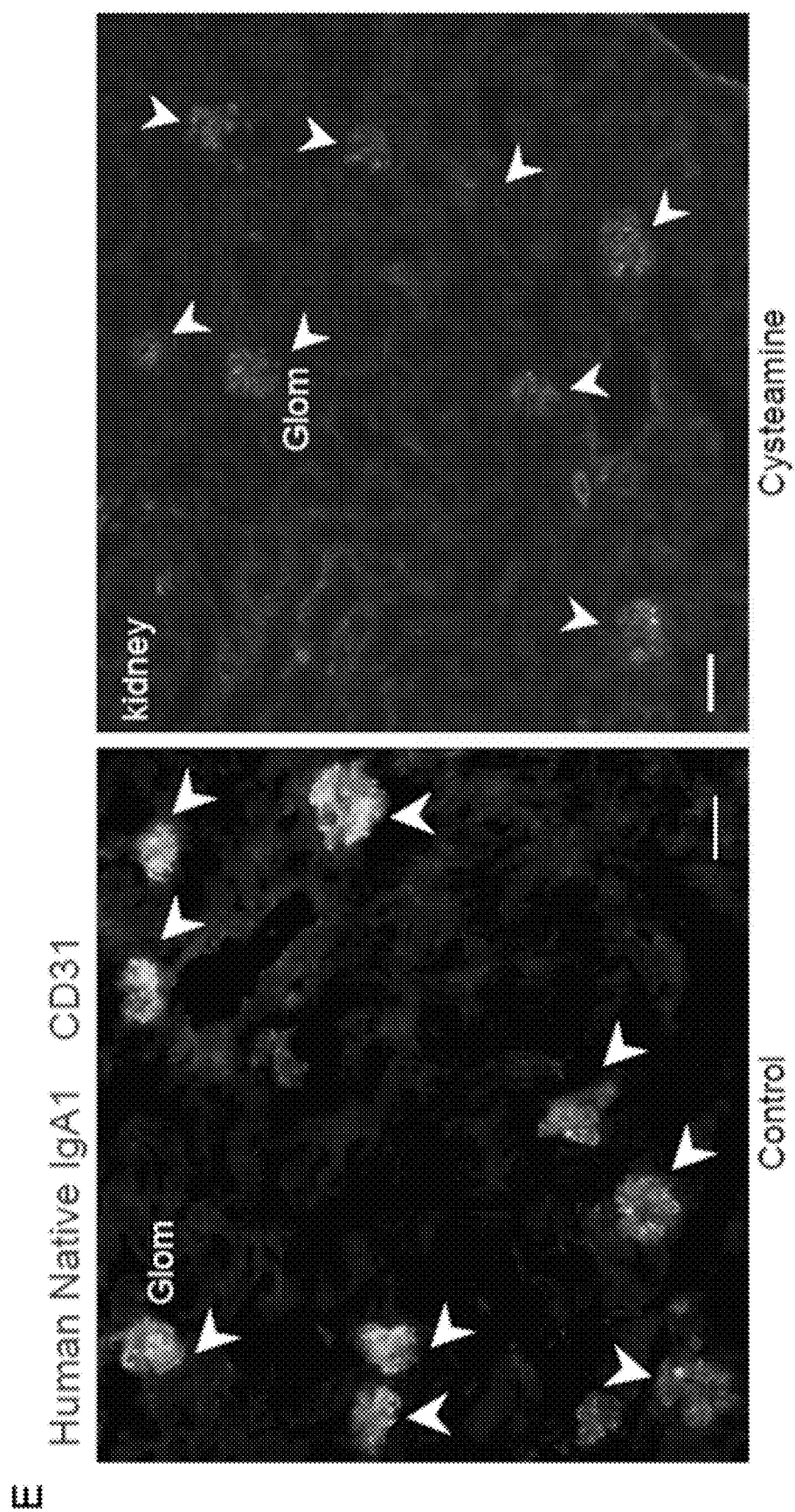
Figure 6:
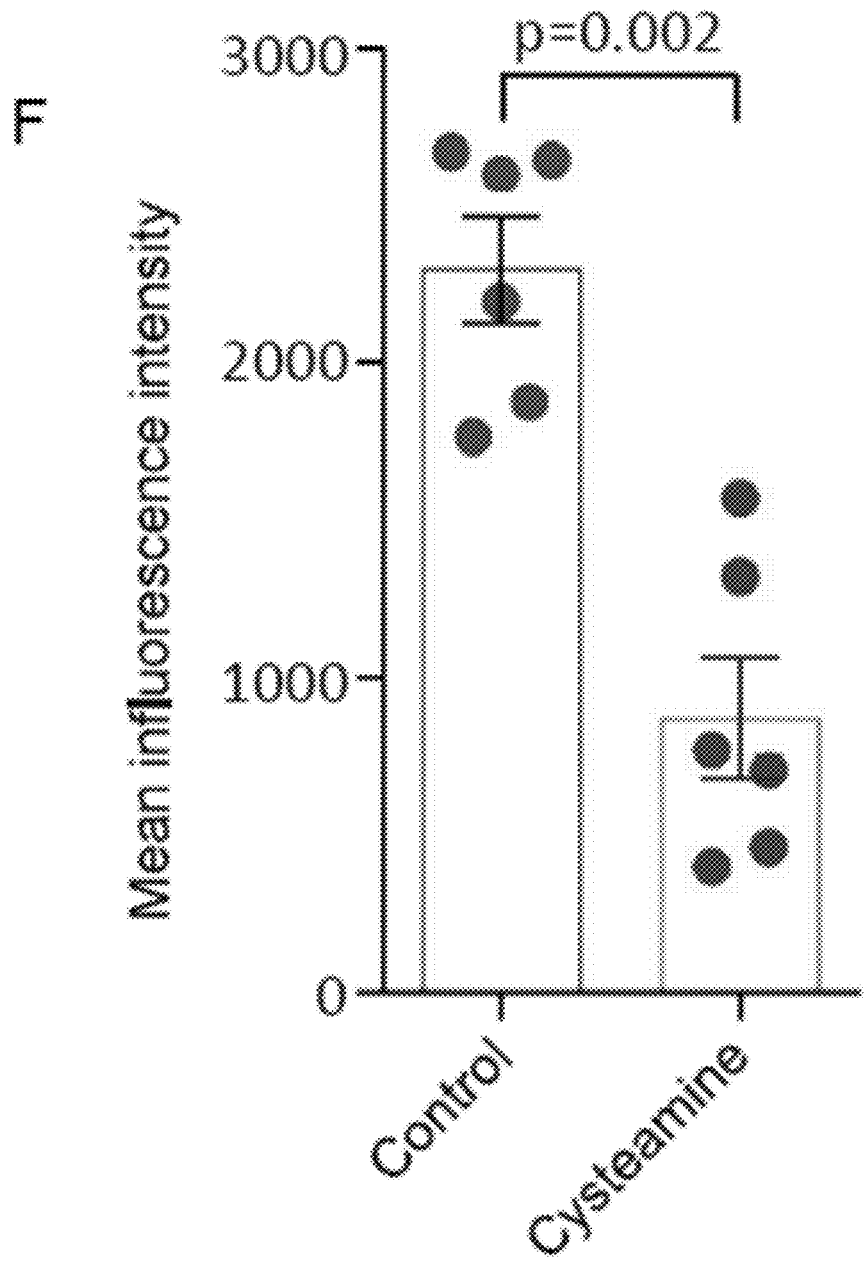

In Vivo Treatment with Cysteamine Reduces Glomerular Mesangial IgA Deposition in Murine Models It was sought to test the in vivo efficacy of cysteamine in a rat model of IgA deposition. A passive induction model was used with 5 daily i.v. injections of purified recombinant rat rIgA (SEQ ID NO.:2) in rats (FIG. 6, part A, left panel). Rats developed prominent IgA deposition in the glomerulus (FIG. 6, part B, top panel). Meanwhile, rats that also received subcutaneous doses of cysteamine two hours prior to each rIgA injection (FIG. 6, part A, right panel) showed less glomerular deposition (FIG. 6, part B, bottom panel and FIG. 6, part C). In order to confirm that rIgA deposition was attributable to disulfide-connected poly-IgA, and reduction of its signals in the glomerulus by cysteamine treatment was due to disassociation of the complexes, mono-rIgA and poly-rIgA were purified separately by SEC as discussed above. As expected, injection of poly-rIgA fraction resulted in mesangial deposition signals, whereas injection of mono-rIgA fraction did not cause glomerular deposition. In establishing the passive rat model for IgA deposition, 5 mg/kg recombinant rat rIgA, which contained a fraction of poly-rIgA, was i.v. injected daily to 14-week-old male Wistar rats (Charles River Labs) for 5 consecutive days. Every day, 3 rats in each group received a subcutaneous dose of either 250 mg/kg cysteamine or buffer control 2 hours before the rIgA injection. Twenty-four hours after the last injection of rIgA, kidneys were collected for immunofluorescence detection of deposits with goat anti-rat IgA antibody (catalog STAR111, Bio-Rad). Similarly, a passive IgA deposition mouse model was established by injecting 35 mg/kg purified human IgA1 in BALB/c mice (Charles River Labs). Two hours before IgA1 injection, mice in each experimental group each received a pretreatment dose of either 200 mg/kg cysteamine or PBS via subcutaneous injection. Two and a half hours after human IgA1 injection, kidneys were harvested and specimens were stained with FITC-conjugated anti-human IgA antibody (catalog 2050-02, SouthernBiotech).

Next, it was sought to examine treatment response of human IgA to cysteamine. Another passive induction model for IgA deposition was used with injections of human IgA1 in mice. Mouse, unlike human and rat, does not have IgA Fc receptor CD89/FcαR1 that can eliminate poly-IgA complexes by phagocytic cells including the macrophage, neutrophil and Kupffer cells. One-time i.v. injection in mice was performed with total IgA1 purified from human plasma (FIG. 6, part D, left panel). As expected, immunofluorescence staining of kidney specimens showed glomerular deposition of human IgA1, prominently located along capillary loops and in mesangial areas (FIG. 6, part E, left panel). In contrast, pretreatment of mice with a subcutaneous dose of cysteamine at 200 mg/kg.BW two hours prior to IgA injection (FIG. 6, part D, right panel) showed markedly lower glomerular IgA signals (FIG. 6, part E, right panel). Particularly, the broad presence of high intensity IgA1 puncta mostly disappeared in the animals that received this prophylactic dose of cysteamine (FIG. 6, part F). Meanwhile, blood IgA1 levels showed no significant difference between the two groups of mice, demonstrating specific reduction of IgA deposition in the kidney by cysteamine.

The foregoing study investigated structural features of IgA that could potentially make it susceptible to forming high-order complexes and causing IgA nephropathy. Unexpectedly, it was discovered poly-IgA complexes isolated from patients' plasma disassembled by reducing agents, suggesting IgA, and possibly also their non-IgA constituents, interconnected via disulfide bridges. In addition to the cysteine residues that participate disulfides between the pair of IgA heavy chains and between heavy and light chains, there are two additional cysteines, namely cysteine-311 and cysteine-471, involved in linking Secretory Component and J-chain subunits of dimeric IgA, respectively. However, because mono-IgA1 is the main circulatory form in blood, these two cysteine residues are expected to be in their free and reduced forms, and therefore susceptible to oxidation. It was further discovered that cysteine-471 in particular can mediate aberrant self-association of IgA and promote glomerular deposition of the resulting poly-IgA complexes. It was then sought the use of aminothiol drugs, such as cysteamine and WR-1065, to stabilize mono-IgA in preventing poly-IgA-directed kidney deposition. Ex vivo and in vivo results showed that these interventional drugs were efficacious in preventing IgA self-association and its glomerular deposition in rodent models.

Admittedly, it remains unclear as to whether the mechanism-of-action with cysteamine was through disassembling of poly-IgA1 in circulation, or in renal deposits followed by accelerated clearance, or both. Critically and without being bound by any theory of any mechanisms of action, it should also be noted that cysteamine is not a sufficiently potent reducing agent to effectively break existing disulfide bonds (FIG. 5, part D). Instead, therapeutic cysteamine possibly protects free Cys471 of IgA1 via cysteamination to lower its reactivity towards IgA1, or other plasma and matrix proteins. Generally, intermolecular disulfide reactions are stochastic, but that is facilitated by noncovalent interactions between two proteins to position a pair of cysteine residues in proximity, often at interaction interfaces. Therefore, it is conceivable that any normal disulfides that are integral parts of immunoglobulin folds, such as those between IgA heavy chains (as in FIG. 5, part D), or between the heavy chain and the light chain (not tested), could withstand cysteamine treatment. In other words, aberrantly connected disulfide interactions are expected to be more susceptible to the drugs. Nevertheless, alkylating agents that form irreversible bonds with cysteine residues, such as N-ethylmaleimide or iodo-acetamide, risk destabilizing the entire IgA molecule, and may not be desirable for treatment as compared to milder aminothiols such as cysteamine. With regard to the in vivo models in our study, it should be cautioned that they do not fully resemble the clinical development of IgA nephropathy, which typically follows a slow course of progression over a long period of time. This is likely due to patients' chronic exposure to low levels of injurious poly-IgA complexes. In contrast, the passive induction models with bolus doses of exogenous IgA presented spikes of poly-IgA levels in blood, causing acute deposition in the kidney. Because mild aminothiols function through shifting the dynamic equilibrium between free and disulfide cysteines, chronic models that fully phenocopy clinical IgA nephropathy are better choices for evaluating treatment effects.

Although it is discussed that the intrinsic propensity of IgA1 to self-aggregate via intermolecular disulfides, the present findings do not contradict with the established 'galactosylation-centric' theory of IgA nephropathy. Structural evidence suggests that hypo-galactosylated IgA may be prone to self-aggregation. The study suggests that noncovalent coalescence of hypo-galactosylated IgA units in the first place could facilitate disulfide connectivity of IgA tailpiece, which in turn, enhances self-association. Similarly, the well-accepted multi-hit model for the pathogenesis of IgA nephropathy includes antigenicity of Gd-IgA in inciting anti-glycan autoantibodies in promoting IgA immune complexes. It is still plausible that these antibody-antigen interactions bring IgA together for their reactive cysteine-471 to form disulfide bridges with additional serum and/or matrix proteins.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

I claim:

1. A method of treating renal IgA deposition in mammals, the method comprising administering a therapeutically effective amount of a thiol-containing molecule, or a pharmaceutically acceptable salt thereof, to a mammal suffering from or at risk of having IgA nephropathy, wherein the thiol-containing molecule is selected from the group consisting of cysteamine, 2-[(3-aminopropyl) amino] ethanethiol, and N-acetylcysteine.

2. The method of claim 1, wherein the thiol-containing molecule is cysteamine or N-acetylcysteine.

3. The method of claim 1, wherein the thiol-containing molecule is cysteamine.

4. The method of claim 1, wherein the thiol-containing molecule is provided as a pharmaceutically acceptable salt.

5. The method of claim 1, wherein the thiol-containing molecule is provided as a hydrochloride salt or a bitartrate salt.

6. The method of claim 1, wherein the treating comprises the thiol-containing molecule binding with an IgA monomer.

7. The method of claim 6, wherein the IgA monomer is human IgA1, and binding occurs at Cys471.

8. The method of claim 1, wherein the administering is performed one or more times during the day.

9. The method of claim 1, wherein the thiol-containing molecule is administered in a daily amount in the range of 0.1 mg/kg to 400 mg/kg.

10. The method of claim 1, wherein the thiol-containing molecule is administered in a daily amount in the range of 1 mg/kg to 200 mg/kg.

11. The method of claim 1, wherein the thiol-containing molecule is 2-[(3-aminopropyl)amino]ethanethiol.

12. The method of claim 1, wherein the 2-[(3-aminopropyl)amino]ethanethiol is WR-1065.

* * * * *

SEQUENCE LISTING

<160> NUMBER OF SEQ ID NOS: 12

<210> SEQ ID NO 1
<211> LENGTH: 714
<212> TYPE: DNA
<213> ORGANISM: Rattus norvegicus

<400> SEQUENCE: 1

```
agctgctcat tagtatgccg cccccgttta tcgctgcagc gtcctgccct tgaggacctt      60
ttacttggat cggaagcgag cctgacctgc accctgcgcg gcctgaaaga accgaccggc     120
gcggtgttta cctggcagcc gaccaccggc aaagatgcgg tgcagaaaga agcggtgcag     180
gatagctgcg gctgctatac cgtgagcagc gtgctgccgg gctgcgcgga acgctggaac     240
aacggcgaaa cctttacctg caccgcgacc catccggaat ttgaaacccc gctgaccggc     300
gaaattgcga aagtgaccga aaacaccttt ccgccgcagg tgcatctgct gccgccgccg     360
agcgaagaac tggcgctgaa cgaactggtg agcctgacct gcctggtgcg cggctttaac     420
ccgaaagatg tgctggtgcg ctggctgcag ggcaacgaag aactgccgag cgaaagctat     480
ctggtgtttg aaccgctgcg cgaaccgggc gaaggcgcga ttacctatct ggtgaccagc     540
gtgctgcgcg tgagcgcgga aacctggaaa cagggcgcgc agtatagctg catggtgggc     600
catgaagcgc tgccgatgag ctttacccag aaaaccattg atcgcctgag cggcaaaccg     660
accaacgtga acgtgagcgt gattatgagc gaaggcgatg gcatttgcta ttag           714
```

<210> SEQ ID NO 2
<211> LENGTH: 237
<212> TYPE: PRT
<213> ORGANISM: Rattus norvegicus

<400> SEQUENCE: 2

```
Ser Cys Ser Leu Val Cys Arg Pro Arg Leu Ser Leu Gln Arg Pro Ala
1               5                   10                  15

Leu Glu Asp Leu Leu Gly Ser Glu Ala Ser Leu Thr Cys Thr Leu
            20                  25                  30

Arg Gly Leu Lys Glu Pro Thr Gly Ala Val Phe Thr Trp Gln Pro Thr
        35                  40                  45
```

Thr Gly Lys Asp Ala Val Gln Lys Glu Ala Val Gln Asp Ser Cys Gly
 50                  55                  60

Cys Tyr Thr Val Ser Ser Val Leu Pro Gly Cys Ala Glu Arg Trp Asn
 65                  70                  75                  80

Asn Gly Glu Thr Phe Thr Cys Thr Ala Thr His Pro Glu Phe Glu Thr
                 85                  90                  95

Pro Leu Thr Gly Glu Ile Ala Lys Val Thr Glu Asn Thr Phe Pro Pro
            100                 105                 110

Gln Val His Leu Leu Pro Pro Ser Glu Glu Leu Ala Leu Asn Glu
        115                 120                 125

Leu Val Ser Leu Thr Cys Leu Val Arg Gly Phe Asn Pro Lys Asp Val
130                 135                 140

Leu Val Arg Trp Leu Gln Gly Asn Glu Glu Leu Pro Ser Glu Ser Tyr
145                 150                 155                 160

Leu Val Phe Glu Pro Leu Arg Glu Pro Gly Glu Gly Ala Ile Thr Tyr
                165                 170                 175

Leu Val Thr Ser Val Leu Arg Val Ser Ala Glu Thr Trp Lys Gln Gly
            180                 185                 190

Ala Gln Tyr Ser Cys Met Val Gly His Glu Ala Leu Pro Met Ser Phe
        195                 200                 205

Thr Gln Lys Thr Ile Asp Arg Leu Ser Gly Lys Pro Thr Asn Val Asn
210                 215                 220

Val Ser Val Ile Met Ser Glu Gly Asp Gly Ile Cys Tyr
225                 230                 235

```
<210> SEQ ID NO 3
<211> LENGTH: 714
<212> TYPE: DNA
<213> ORGANISM: Rattus norvegicus

<400> SEQUENCE: 3
agctgctcat tagtatgccg cccccgttta tcgctgcagc gtcctgccct tgaggacctt      60
ttacttggat cggaagcgag cctgacctgc accctgcgcg gcctgaaaga accgaccggc     120
gcggtgttta cctggcagcc gaccaccggc aaagatgcgg tgcagaaaga agcggtgcag     180
gatagctgcg gctgctatac cgtgagcagc gtgctgccgg gctgcgcgga acgctggaac     240
aacggcgaaa cctttacctg caccgcgacc catccggaat ttgaaacccc gctgaccggc     300
gaaattgcga aagtgaccga aaacaccttt ccgccgcagg tgcatctgct gccgccgccg     360
agcgaagaac tggcgctgaa cgaactggtg agcctgacct gcctggtgcg cggctttaac     420
ccgaaagatg tgctggtgcg ctggctgcag ggcaacgaag aactgccgag cgaaagctat     480
ctggtgtttg aaccgctgcg cgaaccgggc gaaggcgcga ttacctatct ggtgaccagc     540
gtgctgcgcg tgagcgcgga aacctggaaa cagggcgcgc agtatagctg catggtgggc     600
catgaagcgc tgccgatgag ctttacccag aaaaccattg atcgcctgag cggcaaaccg     660
accaacgtga acgtgagcgt gattatgagc gaaggcgatg cattagcta ttag           714

<210> SEQ ID NO 4
<211> LENGTH: 237
<212> TYPE: PRT
<213> ORGANISM: Rattus norvegicus

<400> SEQUENCE: 4
```

Ser Cys Ser Leu Val Cys Arg Pro Arg Leu Ser Leu Gln Arg Pro Ala
 1               5                  10                  15

Leu Glu Asp Leu Leu Gly Ser Glu Ala Ser Leu Thr Cys Thr Leu
         20                  25                  30

Arg Gly Leu Lys Glu Pro Thr Gly Ala Val Phe Thr Trp Gln Pro Thr
         35                  40                  45

Thr Gly Lys Asp Ala Val Gln Lys Glu Ala Val Gln Asp Ser Cys Gly
 50                  55                  60

Cys Tyr Thr Val Ser Val Leu Pro Gly Cys Ala Glu Arg Trp Asn
 65                  70                  75                  80

Asn Gly Glu Thr Phe Thr Cys Thr Ala Thr His Pro Glu Phe Glu Thr
                 85                  90                  95

Pro Leu Thr Gly Glu Ile Ala Lys Val Thr Glu Asn Thr Phe Pro Pro
                100                 105                 110

Gln Val His Leu Leu Pro Pro Ser Glu Glu Leu Ala Leu Asn Glu
         115                 120                 125

Leu Val Ser Leu Thr Cys Leu Val Arg Gly Phe Asn Pro Lys Asp Val
130                 135                 140

Leu Val Arg Trp Leu Gln Gly Asn Glu Glu Leu Pro Ser Glu Ser Tyr
145                 150                 155                 160

Leu Val Phe Glu Pro Leu Arg Glu Pro Gly Glu Gly Ala Ile Thr Tyr
                165                 170                 175

Leu Val Thr Ser Val Leu Arg Val Ser Ala Glu Thr Trp Lys Gln Gly
                180                 185                 190

Ala Gln Tyr Ser Cys Met Val Gly His Glu Ala Leu Pro Met Ser Phe
                195                 200                 205

Thr Gln Lys Thr Ile Asp Arg Leu Ser Gly Lys Pro Thr Asn Val Asn
        210                 215                 220

Val Ser Val Ile Met Ser Glu Gly Asp Gly Ile Ser Tyr
225                 230                 235

<210> SEQ ID NO 5
<211> LENGTH: 714
<212> TYPE: DNA
<213> ORGANISM: Rattus norvegicus

<400> SEQUENCE: 5
agctgctcat tagtatgccg cccccgttta tcgctgcagc gtcctgccct tgaggacctt      60
ttacttggat cggaagcgag cctgacctgc accctgcgcg gcctgaaaga ccgaccggc     120 gcggtgttta cctggcagcc gaccaccggc aaagatgcgg tgcagaaaga agcggtgcag     180
gatagctgcg gctgctatac cgtgagcagc gtgctgccgg gctccgcgga acgctggaac     240
aacggcgaaa cctttacctg caccgcgacc catccggaat ttgaaacccc gctgaccggc     300
gaaattgcga agtgaccga aaacacctt ccgccgcagg tgcatctgct gccgccgccg     360
agcgaagaac tggcgctgaa cgaactggtg agcctgacct gcctggtgcg cggctttaac     420
ccgaaagatg tgctggtgcg ctggctgcag ggcaacgaag aactgccgag cgaaagctat     480
ctggtgtttg aaccgctgcg cgaaccgggc gaaggcgcga ttacctatct ggtgaccagc     540
gtgctgcgcg tgagcgcgga aacctggaaa cagggcgcgc agtatagctg catggtgggc     600
catgaagcgc tgccgatgag ctttacccag aaaaccattg atcgcctgag cggcaaaccg     660
accaacgtga acgtgagcgt gattatgagc gaaggcgatg gcatttgcta ttag     714

<210> SEQ ID NO 6
<211> LENGTH: 237
<212> TYPE: PRT
<213> ORGANISM: Rattus norvegicus

<400> SEQUENCE: 6

```
Ser Cys Ser Leu Val Cys Arg Pro Arg Leu Ser Leu Gln Arg Pro Ala
1               5                   10                  15
Leu Glu Asp Leu Leu Leu Gly Ser Glu Ala Ser Leu Thr Cys Thr Leu
            20                  25                  30
Arg Gly Leu Lys Glu Pro Thr Gly Ala Val Phe Thr Trp Gln Pro Thr
        35                  40                  45
Thr Gly Lys Asp Ala Val Gln Lys Glu Ala Val Gln Asp Ser Cys Gly
    50                  55                  60
Cys Tyr Thr Val Ser Ser Val Leu Pro Gly Ser Ala Glu Arg Trp Asn
65                  70                  75                  80
Asn Gly Glu Thr Phe Thr Cys Thr Ala Thr His Pro Glu Phe Glu Thr
                85                  90                  95
Pro Leu Thr Gly Glu Ile Ala Lys Val Thr Glu Asn Thr Phe Pro Pro
            100                 105                 110
Gln Val His Leu Leu Pro Pro Ser Glu Glu Leu Ala Leu Asn Glu
        115                 120                 125
Leu Val Ser Leu Thr Cys Leu Val Arg Gly Phe Asn Pro Lys Asp Val
145                 150                 155                 160
Leu Val Arg Trp Leu Gln Gly Asn Glu Glu Leu Pro Ser Glu Ser Tyr
145                 150                 155                 160
Leu Val Phe Glu Pro Leu Arg Glu Pro Gly Glu Ala Ile Thr Tyr
            165                 170                 175
Leu Val Thr Ser Val Leu Arg Val Ser Ala Glu Thr Trp Lys Gln Gly
            180                 185                 190
Ala Gln Tyr Ser Cys Met Val Gly His Glu Ala Leu Pro Met Ser Phe
        195                 200                 205
Thr Gln Lys Thr Ile Asp Arg Leu Ser Gly Lys Pro Thr Asn Val Asn
    210                 215                 220
Val Ser Val Ile Met Ser Glu Gly Asp Gly Ile Cys Tyr
225                 230                 235
```

<210> SEQ ID NO 7
<211> LENGTH: 714
<212> TYPE: DNA
<213> ORGANISM: Rattus norvegicus

<400> SEQUENCE: 7

```
agctgctcat tagtatgccg ccccgtttta tcgctgcagc gtcctgccct tgaggacctt      60
ttacttggat cggaagcgag cctgacctgc accctgcgcg gcctgaaaga accgaccggc     120
gcggtgttta cctggcagcc gaccaccggc aaagatgcgg tgcagaaaga agcggtgcag     180
gatagctgcg gctgctatac cgtgagcagc gtgctgccgg gctccgcgga acgctggaac     240
aacggcgaaa cctttacctg caccgcgacc catccggaat tgaaaccccc gctgaccggc     300
gaaattgcga aagtgaccga aaacaccttt ccgccgcagg tgcatctgct gccgccgccg     360
agcgaagaac tggcgctgaa cgaactggtg agcctgacct gcctggtgcg cggctttaac     420
ccgaaagatg tgctggtgcg ctggctgcag ggcaacgaag aactgccgag cgaaagctat     480
ctggtgtttg aaccgctgcg cgaaccgggc gaaggcgcga ttacctatct ggtgaccagc     540
gtgctgcgcg tgagcgcgga aacctggaaa cagggcgcgc agtatagctg catggtgggc     600
catgaagcgc tgccgatgag ctttacccag aaaaccattg atcgcctgag cggcaaaccg     660
accaacgtga acgtgagcgt gattatgagc gaaggcgatg gcattagcta ttag           714
```

<210> SEQ ID NO 8
<211> LENGTH: 237
<212> TYPE: PRT
<213> ORGANISM: Rattus norvegicus

<400> SEQUENCE: 8

Ser Cys Ser Leu Val Cys Arg Pro Arg Leu Ser Leu Gln Arg Pro Ala
1               5                   10                  15

Leu Glu Asp Leu Leu Gly Ser Glu Ala Ser Leu Thr Cys Thr Leu
            20                  25                  30

Arg Gly Leu Lys Glu Pro Thr Gly Ala Val Phe Thr Trp Gln Pro Thr
        35                  40                  45

Thr Gly Lys Asp Ala Val Gln Lys Glu Ala Val Gln Asp Ser Cys Gly
    50                  55                  60

Cys Tyr Thr Val Ser Ser Val Leu Pro Gly Ser Ala Glu Arg Trp Asn
65                  70                  75                  80

Asn Gly Glu Thr Phe Thr Cys Thr Ala Thr His Pro Glu Phe Glu Thr
                85                  90                  95

Pro Leu Thr Gly Glu Ile Ala Lys Val Thr Glu Asn Thr Phe Pro Pro
            100                 105                 110

Gln Val His Leu Leu Pro Pro Ser Glu Glu Leu Ala Leu Asn Glu
        115                 120                 125

Leu Val Ser Leu Thr Cys Leu Val Arg Gly Phe Asn Pro Lys Asp Val
145                 150                 155                 160

Leu Val Arg Trp Leu Gln Gly Asn Glu Glu Leu Pro Ser Glu Ser Tyr
145                 150                 155                 160

Leu Val Phe Glu Pro Leu Arg Glu Pro Gly Glu Gly Ala Ile Thr Tyr
                165                 170                 175

Leu Val Thr Ser Val Leu Arg Val Ser Ala Glu Thr Trp Lys Gln Gly
            180                 185                 190

Ala Gln Tyr Ser Cys Met Val Gly His Glu Ala Leu Pro Met Ser Phe
        195                 200                 205

Thr Gln Lys Thr Ile Asp Arg Leu Ser Gly Lys Pro Thr Asn Val Asn
    210                 215                 220

Val Ser Val Ile Met Ser Glu Gly Asp Gly Ile Ser Tyr
225                 230                 235

<210> SEQ ID NO 9
<211> LENGTH: 702
<212> TYPE: DNA
<213> ORGANISM: Homo sapiens

<400> SEQUENCE: 9
agctgctgcc atccgcgctt atcgcttcac cgccctgcat tggaggattt gttacttggt     60
tcagaggcca atctgacgtg taccctgacc ggcctgcgcg atgcgagcgg cgtgaccttt    120
acctggaccc cgagcagcgg caaaagcgcg gtgcagggcc cgccggaacg cgatctgtgc    180
ggctgctata gcgtgagcag cgtgctgccg ggctgcgcgg aaccgtggaa ccacggcaaa    240
acctttacct gcaccgcggc gtatccggaa agcaaaaccc cgctgaccgc gaccctgagc    300
aaaagcggca acacctttcg cccggaagtg catctgctgc cgccgccgag cgaagaactg    360
gcgctgaacg aactggtgac cctgacctgc ctggcgcgcg gctttagccc gaaagatgtg    420
ctggtgcgct ggctgcaggg cagccaggaa ctgccgcgcg aaaaatatct gacctgggcg    480
agccgccagg aaccgagcca gggcaccacc acctttgcgg tgaccagcat tctgcgcgtg    540

```
gcggcggaag attggaaaaa aggcgatacc tttagctgca tggtgggcca tgaagcgctg    600
ccgctggcgt ttacccagaa aaccattgat cgcctggcgg gcaaaccgac ccatgtgaac    660
gtgagcgtgg tgatggcgga agtggatggc acctgctatt ag                       702
```

```
<210> SEQ ID NO 10
<211> LENGTH: 233
<212> TYPE: PRT
<213> ORGANISM: Homo sapiens

<400> SEQUENCE: 10
```

```
Ser Cys Cys His Pro Arg Leu Ser Leu His Arg Pro Ala Leu Glu Asp
1               5                   10                  15

Leu Leu Leu Gly Ser Glu Ala Asn Leu Thr Cys Thr Leu Thr Gly Leu
            20                  25                  30

Arg Asp Ala Ser Gly Val Thr Phe Thr Trp Thr Pro Ser Ser Gly Lys
        35                  40                  45

Ser Ala Val Gln Gly Pro Pro Glu Arg Asp Leu Cys Gly Cys Tyr Ser
    50                  55                  60

Val Ser Ser Val Leu Pro Gly Cys Ala Glu Pro Trp Asn His Gly Lys
65                  70                  75                  80

Thr Phe Thr Cys Thr Ala Ala Tyr Pro Glu Ser Lys Thr Pro Leu Thr
                85                  90                  95

Ala Thr Leu Ser Lys Ser Gly Asn Thr Phe Arg Pro Glu Val His Leu
            100                 105                 110

Leu Pro Pro Pro Ser Glu Glu Leu Ala Leu Asn Glu Leu Val Thr Leu
        115                 120                 125

Thr Cys Leu Ala Arg Gly Phe Ser Pro Lys Asp Val Leu Val Arg Trp
    130                 135                 140

Leu Gln Gly Ser Gln Glu Leu Pro Arg Glu Lys Tyr Leu Thr Trp Ala
145                 150                 155                 160

Ser Arg Gln Glu Pro Ser Gln Gly Thr Thr Thr Phe Ala Val Thr Ser
                165                 170                 175

Ile Leu Arg Val Ala Ala Glu Asp Trp Lys Lys Gly Asp Thr Phe Ser
            180                 185                 190

Cys Met Val Gly His Glu Ala Leu Pro Leu Ala Phe Thr Gln Lys Thr
        195                 200                 205

Ile Asp Arg Leu Ala Gly Lys Pro Thr His Val Asn Val Ser Val Val
    210                 215                 220

Met Ala Glu Val Asp Gly Thr Cys Tyr
225                 230
```

```
<210> SEQ ID NO 11
<211> LENGTH: 702
<212> TYPE: DNA
<213> ORGANISM: Homo sapiens

<400> SEQUENCE: 11
agctgctgcc atccgcgctt atcgcttcac cgccctgcat tggaggattt gttacttggt    60
tcagaggcca atctgacgtg taccctgacc ggcctgcgcg atgcgagcgg cgtgaccttt   120
acctggaccc cgagcagcgg caaaagcgcg gtgcagggcc cgccggaacg cgatctgtgc   180
ggctgctata gcgtgagcag cgtgctgccg ggctgcgcgg aaccgtggaa ccacggcaaa   240
acctttacct gcaccgcggc gtatccggaa agcaaaaccc cgctgaccgc gaccctgagc   300
aaaagcggca acacctttcg cccggaagtg catctgctgc cgccgccgag cgaagaactg   360
```

```
gcgctgaacg aactggtgac cctgacctgc ctggcgcgcg gctttagccc gaaagatgtg    420
ctggtgcgct ggctgcaggg cagccaggaa ctgccgcgcg aaaaatatct gacctgggcg    480
agccgccagg aaccgagcca gggcaccacc acctttgcgg tgaccagcat tctgcgcgtg    540
gcggcggaag attggaaaaa aggcgatacc tttagctgca tggtgggcca tgaagcgctg    600
ccgctggcgt ttacccagaa aaccattgat cgcctggcgg gcaaaccgac ccatgtgaac    660
gtgagcgtgg tgatggcgga agtggatggc accagctatt ag                      702

<210> SEQ ID NO 12
<211> LENGTH: 233
<212> TYPE: PRT
<213> ORGANISM: Homo sapiens

<400> SEQUENCE: 12

Ser Cys Cys His Pro Arg Leu Ser Leu His Arg Pro Ala Leu Glu Asp
1               5                   10                  15

Leu Leu Leu Gly Ser Glu Ala Asn Leu Thr Cys Thr Leu Thr Gly Leu
            20                  25                  30

Arg Asp Ala Ser Gly Val Thr Phe Thr Trp Thr Pro Ser Ser Gly Lys
        35                  40                  45

Ser Ala Val Gln Gly Pro Pro Glu Arg Asp Leu Cys Gly Cys Tyr Ser
    50                  55                  60

Val Ser Ser Val Leu Pro Gly Cys Ala Glu Pro Trp Asn His Gly Lys
65                  70                  75                  80

Thr Phe Thr Cys Thr Ala Ala Tyr Pro Glu Ser Lys Thr Pro Leu Thr
                85                  90                  95

Ala Thr Leu Ser Lys Ser Gly Asn Thr Phe Arg Pro Glu Val His Leu
            100                 105                 110

Leu Pro Pro Pro Ser Glu Glu Leu Ala Leu Asn Glu Leu Val Thr Leu
        115                 120                 125

Thr Cys Leu Ala Arg Gly Phe Ser Pro Lys Asp Val Leu Val Arg Trp
    130                 135                 140

Leu Gln Gly Ser Gln Glu Leu Pro Arg Glu Lys Tyr Leu Thr Trp Ala
145                 150                 155                 160

Ser Arg Gln Glu Pro Ser Gln Gly Thr Thr Thr Phe Ala Val Thr Ser
                165                 170                 175

Ile Leu Arg Val Ala Ala Glu Asp Trp Lys Lys Gly Asp Thr Phe Ser
            180                 185                 190

Cys Met Val Gly His Glu Ala Leu Pro Leu Ala Phe Thr Gln Lys Thr
        195                 200                 205

Ile Asp Arg Leu Ala Gly Lys Pro Thr His Val Asn Val Ser Val Val
    210                 215                 220

Met Ala Glu Val Asp Gly Thr Ser Tyr
225                 230
```